United States Patent
Yang et al.

(10) Patent No.: US 9,162,977 B2
(45) Date of Patent: *Oct. 20, 2015

(54) SYNTHETIC ION CHANNELS

(71) Applicant: The University of Hong Kong, Hong Kong (CN)

(72) Inventors: Dan Yang, Hong Kong (CN); Xiang Li, Hong Kong (CN); Huiyan Zha, Toronto (CA)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 235 days.

This patent is subject to a terminal disclaimer.

(21) Appl. No.: 13/731,971

(22) Filed: Dec. 31, 2012

(65) Prior Publication Data

US 2013/0244944 A1 Sep. 19, 2013

Related U.S. Application Data

(63) Continuation-in-part of application No. 11/959,482, filed on Dec. 19, 2007, now Pat. No. 8,378,138.

(60) Provisional application No. 60/876,012, filed on Dec. 19, 2006.

(51) Int. Cl.
| | | |
|---|---|---|
| C07C 239/08 | (2006.01) |
| C07C 335/16 | (2006.01) |
| C07K 5/062 | (2006.01) |
| C07C 259/06 | (2006.01) |
| C07C 275/28 | (2006.01) |
| C07D 213/79 | (2006.01) |
| C07D 213/81 | (2006.01) |
| C07C 239/20 | (2006.01) |
| C07D 213/63 | (2006.01) |
| C07C 271/22 | (2006.01) |
| C07C 237/22 | (2006.01) |

(52) U.S. Cl.
CPC ............ *C07C 335/16* (2013.01); *C07C 237/22* (2013.01); *C07C 239/20* (2013.01); *C07C 259/06* (2013.01); *C07C 271/22* (2013.01); *C07C 275/28* (2013.01); *C07D 213/63* (2013.01); *C07D 213/79* (2013.01); *C07D 213/81* (2013.01); *C07K 5/06034* (2013.01); *C07B 2200/07* (2013.01); *C07C 239/08* (2013.01)

(58) Field of Classification Search
CPC ..................................................... C07C 239/08
USPC .............................. 564/156, 215; 560/76, 312
See application file for complete search history.

(56) References Cited

PUBLICATIONS

Abo-Ghalia M. et al., Amino Acids, 2004, vol. 26, No. 3, pp. 283-289.*
Hassan Saad S. M. et al., Analytica Chimica Acta, 2003, vol. 482, No. 1, pp. 9-18.*

\* cited by examiner

*Primary Examiner* — Kamal Saeed
*Assistant Examiner* — Janet L Coppins
(74) *Attorney, Agent, or Firm* — Saliwanchik, Lloyd & Eisenschenk

(57) ABSTRACT

Provided herein are self-assembling compounds that can form ion channels in lipid bilayers or cell membranes and ion-channel-forming compositions comprising the self-assembling compounds. Also provided are methods of making and using the ion channels formed from a plurality of molecules of the self-assembling compounds. Further, provided are methods of treating or preventing conditions and diseases that are related to the dysfunction of ion channels, including chloride channels.

34 Claims, 10 Drawing Sheets unimolecular     barrel-stave     barrel-hoop     barrel-rosette

SYNTHETIC ION CHANNELS

PRIOR RELATED APPLICATIONS

This application is a continuation-in-part application of Ser. No. 11/959,482, filed Dec. 19, 2007, which claims the benefit of U.S. Provisional Application Ser. No. 60/876,012, filed Dec. 19, 2006, each of which is hereby incorporated by reference herein in its entirety.

FEDERALLY SPONSORED RESEARCH STATEMENT

Not applicable.

REFERENCE TO MICROFICHE APPENDIX

Not applicable.

FIELD

Provided herein are self-assembling compounds which can form ion channels in lipid bilayers or cell membranes, ion-channel-forming compositions comprising the compounds, pharmaceutical compositions comprising the compounds and methods of making and using the compounds and compositions. Also provided herein are methods of forming a synthetic anion channel in a lipid bilayer or a cell membrane. Further provided herein are methods of treating, preventing and/or managing a disease that is related to the dysfunction of chloride channel, and methods of mediating the flow of chloride ions across membranes of liposomes and living cells by using the self-assembling compounds disclosed herein.

BACKGROUND

Ion transport across cell membranes or lipid bilayers is an important biological process. Ion channels that selectively regulate ion flows are involved in many physiological processes including, but not limited to, neuronal signaling, muscle contraction, cardiovascular function and immune response. A natural ion channel can be an integral membrane protein or more typically an assembly of several proteins which closely packed around a water-filled pore through lipid bilayer. The two key properties of natural ion channels are ion selectivity and gating. Ion selectivity refers to a channel selectively permits only certain ionic species to flow through its pore whereas gating refers to the mechanism of channel opening and closing. Anion channels are generally proteinaceous pores in biological membranes that allow the passive diffusion of anions along their electrochemical gradient. Although these channels may conduct other anions such as iodide or nitrate, they are often called chloride channels because chloride is the most abundant anion in organisms and therefore, the predominant permeating species under most circumstances.

The functions of chloride channels include, but not limited to, ion homeostasis, cell volume regulation, transepithelial transport, and regulation of electrical excitability. Therefore, dysfunction of chloride channels has been implicated in some conditions and diseases related to the impairment of the above-mentioned functions. Some non-limiting examples of such human diseases include cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy and osteopetrose. Consequently, chloride channels have become significant targets for drug discovery. Small molecules that selectively regulate or mimic the functions of chloride channels are potentially useful for the treatment of human diseases such as those mentioned above. Given the significant physiological value of chloride channels, it is desirable to understand how to modulate the functions of chloride channels.

Synthetic ion channels that can mimic the functions of natural ion channels may be used as models to gain insights into the properties of natural ion channels. Hence, discovery of novel synthetic ion channels may lead to new compounds or compositions useful for treating or preventing conditions and diseases where ion transport plays a role. These synthetic channels may potentially be used to control ion flows in biological systems. While many efforts have been focused on the models of cation channels, there are only a few synthetic anion channels, especially chloride channels, reported. Most of the synthetic chloride channels generally have relatively complicated structures and high molecular weights, both of which can restrict their applications in drug discovery. Therefore, there are still needs for novel synthetic ion channel compounds that can be used to treat or prevent conditions and diseases that are related to the dysfunction of ion channels, including chloride channels.

SUMMARY

Provided herein are compounds that may self-assemble to form ion channels in lipid bilayers or cell membranes without the assistance of an outside source, ion-channel compositions comprising the compounds, and methods of making and using same for treating, managing or preventing a disease that is related to the dysfunction of chloride channel. In certain embodiments, the compounds may assemble to form ion channels with the assistance of an internal or external physical force such as electromagnetic radiation (e.g., X-ray, UV light, visible light, microwave or IR radiation), electric field, magnetic field, ultrasound, audio sound, heat or pressure. In certain embodiments, the compounds may assemble to form ion channels with the assistance of a polar compound, such as acids, bases and the like, or a non-polar compound, such as hydrocarbons and the like. Also provided herein are biological and synthetic membranes having synthetic anion channels comprising the self-assembling compounds. In certain embodiments, the compounds are self-assembling compounds that self-assemble to form ion channels in lipid bilayers or cell membranes. In certain embodiments, the ion channels are anion channels. Further provided are methods for designing synthetic ion channels comprising the step of self-assembling small molecules through hydrogen bonds to form synthetic ion channels.

In one aspect, provided herein are self-assembling compounds represented by formula (I):

(I)

wherein X is an unsubstituted or substituted hydrocarbyl or heterocyclyl;

n is an integer from 1 to 6;

Y is a monovalent, divalent, trivalent, tetravalent, pentavalent or hexavalent linking group formed by removing one, two, three, four, five and six hydrogen atoms respectively from an unsubstituted or substituted hydrocarbon (e.g., alkane, alkene and alkyne), carbocycle (e.g., aliphatic carbocycle such as cyclohexane, or arene such as benzene) or heterocycle (e.g., heteroarene such as pyridine); and $H_{DA}$ is a divalent group comprising at least a hydrogen bond donor and at least a hydrogen bond acceptor for self-assembly through hydrogen bonds to form at least an ion channel.

In some embodiments, $H_{DA}$ of formula (I) is a divalent group having formula (II):

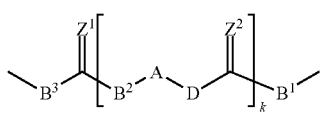

(II)

wherein each of $Z^1$ and $Z^2$ is independently O, S or $NR^1$;

each of A, $B^1$, $B^2$, $B^3$ and D is independently a bond, O, S, $NR^2$ or a substituted or unsubstituted $C_{1-10}$ alkylene; and k is an integer from 1 to 20, where each of $R^1$ and $R^2$ is independently H, acyl, hydrocarbyl, carbocyclyl or heterocyclyl and at least one of $B^1$ and $B^2$ is NH.

In other embodiments, $H_{DA}$ of formula (I) is represented by formula (III):

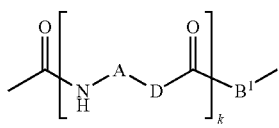

(III)

wherein k is an integer from 1 to 20;

A is a bond, O, S, $NR^2$ or a substituted or unsubstituted $C_{1-10}$alkylene where $R^2$ is H, acyl, hydrocarbyl, carbocyclyl or heterocyclyl;

$B^1$ is O or NH; and

D is $C_{1-3}$ alkylene or $C_{1-3}$ alkylene substituted with one or more hydrocarbyl or heterocyclyl.

In certain embodiments, $H_{DA}$ of formula (I) is represented by formula (IV):

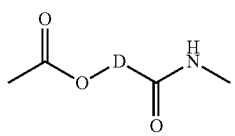

(IV)

wherein D is $C_{1-3}$ alkylene or $C_{1-3}$ alkylene substituted with one or more hydrocarbyl or heterocyclyl.

In certain embodiments, $H_{DA}$ of formula (I) is represented by formula (IVB):

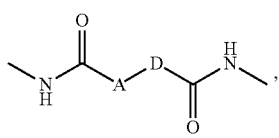

(IVB)

wherein A is a bond, O, S, $NR^2$ or a substituted or unsubstituted $C_{1-10}$ alkylene where $R^2$ is H, acyl, hydrocarbyl, carbocyclyl or heterocyclyl; and D is $C_{1-3}$ alkylene or $C_{1-3}$ alkylene substituted with one or more hydrocarbyl or heterocyclyl.

In some embodiments, n of formula (I) of the self-assembling compound disclosed herein is 1. In other embodiments, n is 2 or 3, and at least two of the $X-H_{DA}$ units are the same. In further embodiments, n is 2 or 3, and at least two of the $X-H_{DA}$ units are different.

In some embodiments, X of formula (I) of the self-assembling compound disclosed herein is hydrocarbyl or substituted hydrocarbyl. In other embodiments, X is hydrocarbyl or substituted hydrocarbyl comprising 1 to 14 carbon atoms. In further embodiments, X is alkyl or substituted alkyl having 1 to 14 carbon atoms. In still further embodiments, X is isobutyl.

In some embodiments, Y of formula (I) of the self-assembling compound disclosed herein is a divalent or trivalent linking group formed by removing two or three hydrogen atoms respectively from an unsubstituted or substituted alkane, alkene or alkyne. In other embodiments, Y is a divalent or trivalent linking group formed by removing two or three hydrogen atoms respectively from an unsubstituted or substituted $C_{2-12}$ alkane, alkene or alkyne. In further embodiments, Y is unsubstituted or substituted propylene or propenylene.

In certain embodiments, Y of formula (I) of the self-assembling compound disclosed herein is a divalent or trivalent linking group formed by removing two or three hydrogen atoms respectively from an unsubstituted or substituted monocyclic, bicyclic or tricyclic aromatic carbocycle. In other embodiments, Y is a divalent or trivalent linking group formed by removing two or three hydrogen atoms respectively from an unsubstituted or substituted arene such as benzene.

In some embodiments, Y of formula (I) of the self-assembling compound disclosed herein is a divalent or trivalent linking group formed by removing two or three hydrogen atoms respectively from an unsubstituted or substituted monocyclic, bicyclic or tricyclic heterocycle. In other embodiments, Y is a divalent or trivalent linking group formed by removing two or three hydrogen atoms respectively from an unsubstituted or substituted heteroarene such as pyridine.

In certain embodiments, $H_{DA}$ of formula (I) of the self-assembling compound disclosed herein comprises at least one primary amide or secondary amide group.

In some embodiments, D of formula (II), (IV) or (IVB) is $C_{1-3}$ alkylene substituted with at least an alkyl, aryl, substituted alkyl or substituted aryl group. In other embodiments, D is $C_{1-3}$ alkylene substituted with at least an isobutyl group. In still further embodiments, D is methylene substituted with an isobutyl.

In certain embodiments, A of formula (II) or (III) is a bond; D is methylene or substituted methylene; and k is 1. In further embodiments, A of formula (II) or (III) is O; D is methylene or substituted methylene; and k is 1. In still further embodiments, Y is arylene, heteroarylene, alkylene or alkenylene; and each X is an unsubstituted or substituted hydrocarbyl having 1 to 14 carbon atoms.

In some embodiments, the self-assembling compound disclosed herein is:
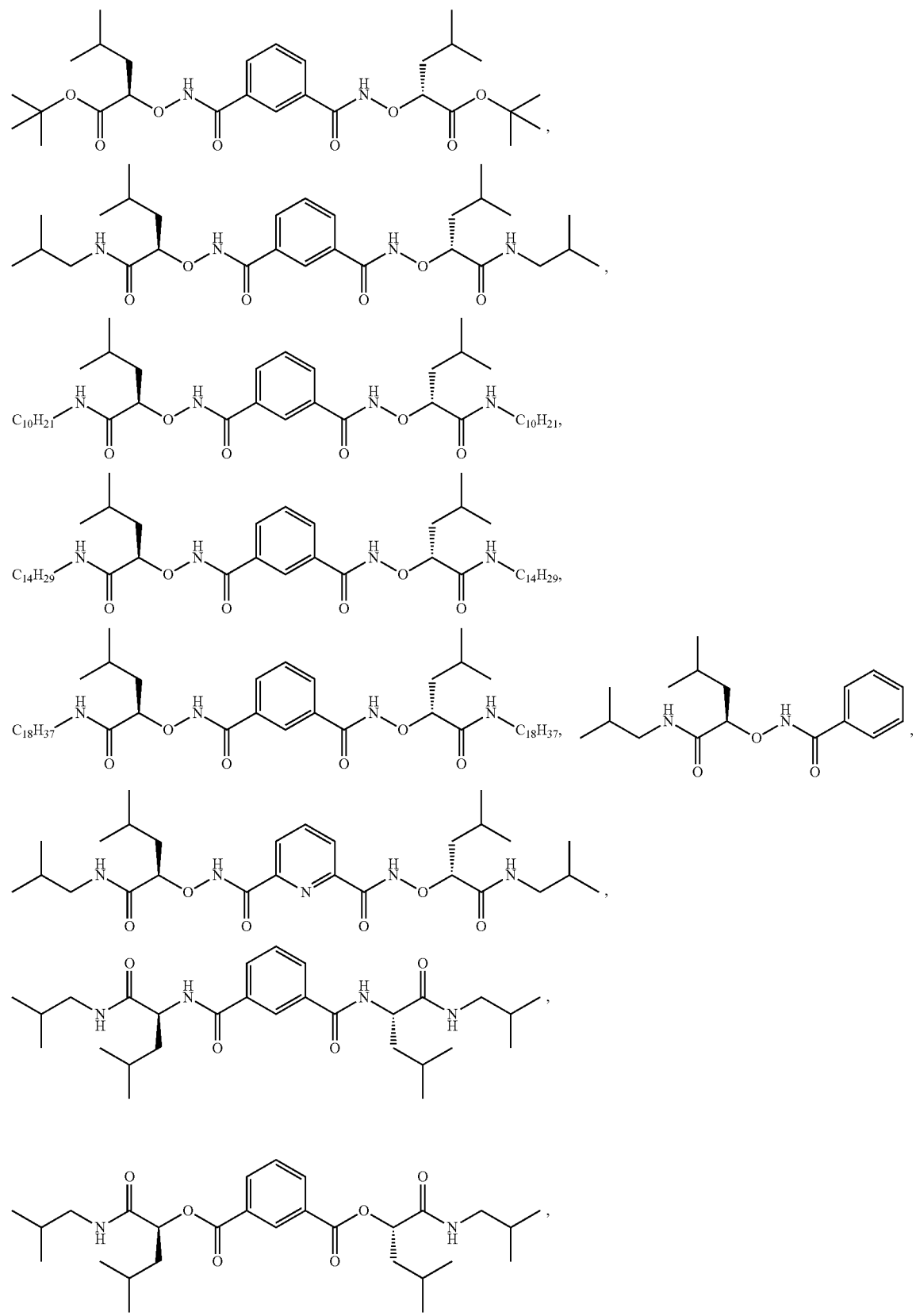

-continued

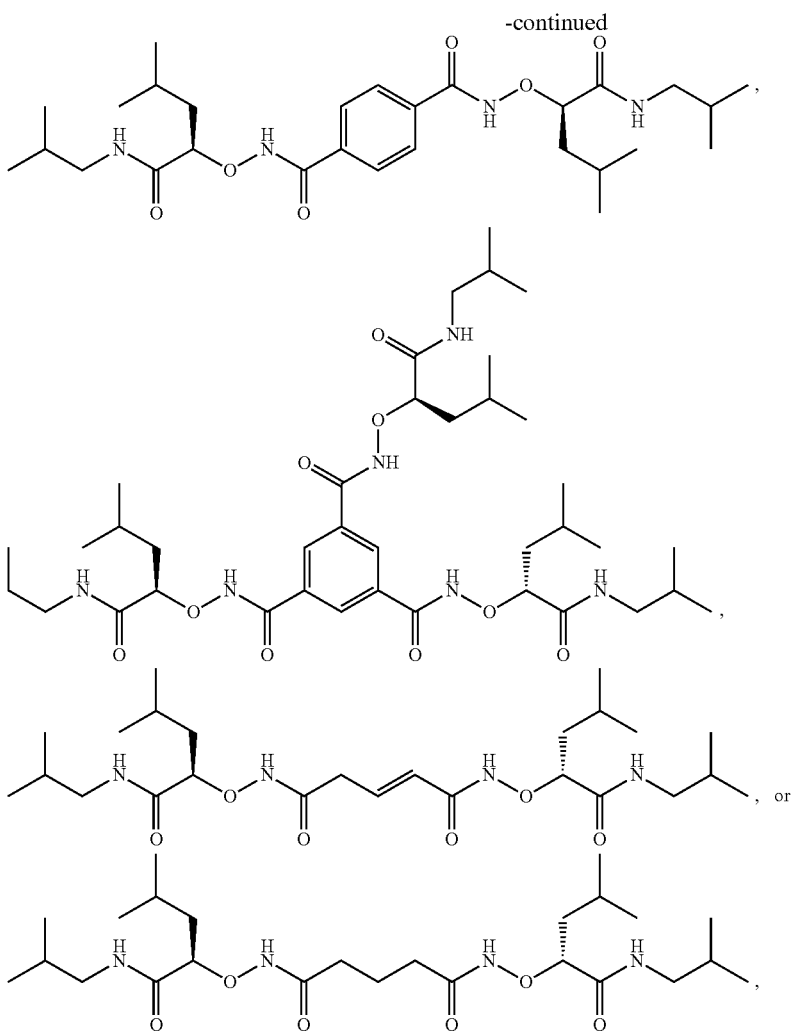

or a salt, solvate, polymorph or stereoisomer thereof.

In further embodiments, the self-assembling compound is

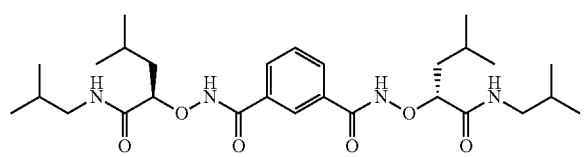

or a salt, solvate, polymorph or stereoisomer thereof

In another aspect, provided herein is an ion-channel composition comprising a lipid bilayer or a cell membrane, and a plurality of molecules of the self-assembling compounds disclosed herein wherein the molecules form an anion channel across the thickness of the membrane. In some embodiments, the plurality of molecules self-assemble to form an anion channel across the thickness of the lipid bilayer. In further embodiments, the anion channel is a fluoride, chloride, bromide, iodide, nitrate, nitrite, sulfate, bisulfate, carbonate, bicarbonate, phosphate, hydrogen phosphate, dihydrogen phosphate or acetate channel. In still further embodiments, the anion channel is a chloride channel.

In another aspect, provided herein is a method of forming a synthetic anion channel in a lipid bilayer or a cell membrane, the method comprising combining the membrane with a plurality of molecules of the self-assembling compounds disclosed herein which self-assemble to form the anion channel.

In another aspect, provided herein is a method of modulating the flow of anions through a lipid bilayer or a cell membrane, the method comprising the steps of forming an anion channel in the membrane from a plurality of molecules of the self-assembling compounds disclosed herein; and thereafter imposing an anion gradient or a membrane potential.

In another aspect, provided herein is a method of making a synthetic ion channel in a cell membrane comprising the steps of providing a plurality of molecules of the self-assembling compound disclosed herein; and forming molecular columns in the transverse direction of the membrane and between any two adjacent molecular columns by the self-assembling of the molecules through intermolecular hydrogen bonds in the lateral direction of the membrane. In some embodiments, the cell membrane disclosed herein comprises a lipid bilayer.

In another aspect, provided herein is a method of treating, managing or preventing a disease that is related to the dysfunction of chloride channel, the method comprising administering to a mammal in need of such treatment, management or prevention a therapeutically or prophylactically effective amount of the self-assembling compound disclosed herein or a pharmaceutically acceptable salt, solvate or stereoisomer thereof. In some embodiments, the disease is cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy or osteopetrose. In other embodiments, the self-assembling compound or a pharmaceutically acceptable salt, solvate or stereoisomer thereof is inserted into the lipid bilayer of a cell of the mammal. In further embodiments, the mammal is a human.

In another aspect, provided herein is a pharmaceutical composition comprising the self-assembling compound disclosed herein or a pharmaceutically acceptable salt, solvate, polymorph or stereoisomer thereof in a therapeutically or prophylactically effective amount for treating, managing or preventing a disease that is related to the dysfunction of chloride channel. In some embodiments, the pharmaceutical composition further comprises a carrier. In certain embodiments, the pharmaceutical composition further comprises at least an ingredient selected from the group consisting of excipients, moisturizers, carriers, diluents, metal stearates and combinations thereof. In other embodiments, the pharmaceutical composition is in a single unit dosage form. In further embodiments, the pharmaceutical composition is in a single unit dosage form suitable for inserting into the lipid bilayer of a mammalian cell.

In another aspect, provided herein is an ion channel comprising a plurality of molecules of the self-assembling compound disclosed herein, wherein the ion channel is in a cell membrane.

Other embodiments will be in part apparent and in part pointed out hereinafter.

BRIEF DESCRIPTION OF THE FIGURES

FIG. 4a depicts the chemical structure of Example 2. FIG. 4b depicts the crystal structure of Example 2 in stick representation where carbon, hydrogen, nitrogen and oxygen atoms are represented by grey, white, blue and red sticks respectively. Two eight-membered-ring intramolecular hydrogen bonds having a bond length of 2.13 Å are shown as green dashed lines. FIGS. 4c and 4d depicts the top view and side view respectively of the solid-state packing of Example 2. The CH hydrogen atoms in FIGS. 4c and 4d are omitted for clarity. Intermolecular hydrogen bonds, shown as green solid lines in FIG. 4d, link and align adjacent molecules together to form a pore-structure.

DEFINITIONS

Figure 1:
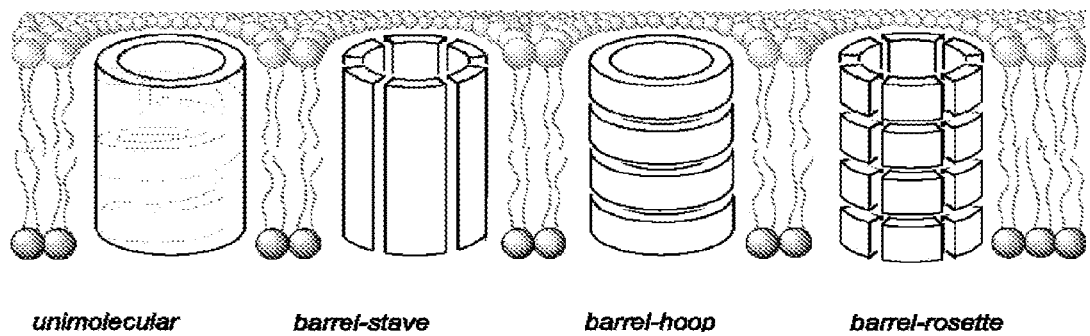
FIG. 1 depicts some classifications of synthetic ion channels based on their structures or "designs."

To facilitate the understanding of the subject matter disclosed herein, a number of terms, abbreviations or other shorthand as used herein are defined below.

Any term, abbreviation or shorthand not defined is understood to have the ordinary meaning used by a skilled artisan contemporaneous with the submission of this application.

"pS" means picoSiemens.

"mM" means millimolar.

"uM" means M=micromolar.

"nM" means nanomolar.

"Anion" means a negatively-charged ion.

"Cation" means a positively-charged ion.

"Bilayer membrane" or "lipid bilayer" refers to a bimolecular thick assembly that forms the permeability barrier surrounding eukaryotic cells and plays a similar role in intracellular compartments, liposomes, and other organelles. This membrane is comprised of any of a large number of amphipathic lipid molecules but in cells it is primarily comprised of phospholipids.

"Cell" refers to prokaryotic cell, yeast cell, eukaryotic cell, plant cell, human cell, animal cell, and in one embodiment, a mammalian cell.

"Membrane" refers to a thin, semi-permeable barrier that separates two liquid phases which may have the same or different compositions.

"Cell membrane" refers to a selectively permeable lipid bilayer coated by proteins. The cell membrane comprises the outer layer of a cell.

"Channel" or "ion channel" refers to an aqueous diffusion pathway for membrane impermeant compounds usually formed by a pore within a cell membrane permitting the transfer of neutral or ionic species through it from one side of the membrane to the other.

"Supramolecular assembly" refers to a well defined complex of molecules held together by noncovalent bonds such as van de Waals force or hydrogen bonds. A supramolecular assembly can comprise two or more molecules. The supramolecular assembly can be in any form or shape such as sphere, cylinder, disk, or sheet which can be solid or hallow. In some embodiments, the supramolecular assembly is in the form of hallow cylinder. In other embodiments, the supramolecular assembly is in the form of a channel with a pore. The dimensions of supramolecular assemblies can range from nanometers to micrometers.

"Self-assembly" refers to the assembly of molecules without guidance or management from an outside source. There are generally two types of self-assembly, intramolecular self-assembly and intermolecular self-assembly. Intramolecular self-assembling molecules are generally complex polymers having the ability to assemble from the random coil conformation into a well-defined stable structure. Intermolecular self-assembly is the ability of molecules to form supramolecular assemblies.

"Self-assembling compound" or "self-assembling molecule" refers to the compound or molecule that can form a supramolecular assembly through a intermolecular self-assembly process.

"Hydrogen bond donor" refers to a group having at least one hydrogen atom attached to a strongly electronegative heteroatom, including oxygen, nitrogen and sulfur.

"Hydrogen bond acceptor" refers to a strongly electronegative heteroatom, including oxygen, nitrogen, sulfur, fluorine, chlorine, and bromine.

"Liposome" refers to an artificial sac, usually spherical, consisting of one (unilamellar) or more (multilamellar) bilayer membranes of phospholipid that encloses an aqueous core and in significant ways mimics biological membranes. The term liposome is sometimes used interchangeably with "vesicle."

"Unilamellar" refers to the bilayer membrane of phospholipid liposomes consists of a single layer.

"Multilamellar" refers to the bilayer membrane of phospholipid liposomes consists of more than one concentric layer, structurally analogous to an onion.

"Selectivity" refers to a measurable preference for one species over another, including cation over anion, anion over cation, one cation over a different cation, or one anion over a different anion.

"Transport" refers to the movement of an ion or other species across a membrane boundary.

"Amino" refers to a primary, secondary, or tertiary amine which may optionally be hydrocarbyl, substituted hydrocarbyl or heteroatom substituted. Specifically included are secondary or tertiary amine nitrogen atoms which are members of a heterocyclic ring. Also specifically included, for example, are secondary or tertiary amino groups substituted by an acyl moiety.

"Alkyl" refers to a fully saturated acyclic monovalent radical containing carbon and hydrogen, and which may be branched or a straight chain. Examples of alkyl groups are methyl, ethyl, n-butyl, t-butyl, n-heptyl, and isopropyl. Unless otherwise indicated, the alkyl groups described herein are preferably lower alkyl containing from one to ten carbon atoms in the principal chain and up to 20 carbon atoms, as exemplified by methyl, ethyl, n-butyl, i-butyl, t-butyl, isoamyl, n-pentyl, and isopentyl.

"Alkenyl" refers to a monovalent or divalent unsaturated, preferably monounsaturated, radical containing carbon and hydrogen, and which may be cyclic, branched or a straight chain. Unless otherwise indicated, the alkenyl groups described herein are preferably lower alkyl containing from two to eight carbon atoms in the principal chain and up to 20 carbon atoms, as exemplified by ethenyl, propenyl, isopropenyl, butenyl, isobutenyl, hexenyl, and the like.

"Alkynyl" refers to a lower alkyl containing from two to eight carbon atoms in the principal chain and up to 20 carbon atoms. They may contain straight or branched chain, as exemplified by ethynyl, propynyl, isopropynyl, butynyl, isobutynyl, hexynyl, and the like.

"Aromatic" refers to aryl or heteroaryl.

"Aryl" refers to optionally substituted carbocyclic aromatic groups, preferably monocyclic or bicyclic groups containing from 6 to 12 carbon atoms in the ring portion, such as phenyl, biphenyl, naphthyl, substituted phenyl, substituted biphenyl or substituted naphthyl. Phenyl and substituted phenyl are the more preferred aryl.

"Halogen" or "halo" refers to fluorine, chlorine, bromine and iodine.

"Heteroatom" shall mean atoms other than carbon and hydrogen.

"Heterocyclo" or "heterocyclyl" refers to optionally substituted, fully saturated or unsaturated, monocyclic or bicyclic, aromatic or nonaromatic groups having at least one heteroatom in at least one ring, and preferably 5 or 6 atoms in each ring. The aromatic heterocyclyl (i.e., heteroaryl) group preferably has 1 or 2 oxygen atoms, 1 or 2 sulfur atoms, and/or 1 to 4 nitrogen atoms in the ring, and may be bonded to the remainder of the molecule through a carbon or heteroatom. Non-limiting examples of heteroaryl include furyl, thienyl, thiazolyl, pyridyl, oxazolyl, pyrrolyl, indolyl, quinolinyl, or isoquinolinyl and the like. Non-limiting examples of substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

"Hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl, alkenyl, alkynyl, and aryl moieties substituted with other aliphatic, cyclic or aryl hydrocarbon groups, such as alkaryl, alkenaryl and alkynaryl. In some embodiments, "hydrocarbon" or "hydrocarbyl" comprises 1 to 20 carbon atoms.

"Hydrocarbylene" is a divalent group formed by removing two hydrogen atoms from a hydrocarbon, the free valencies of which are not engaged in a double bond, e.g. 1,3-phenylene, propane-1,3-diyl, and methylene.

"Substituted" as used herein to describe a compound or chemical moiety means that at least one hydrogen atom of that compound or chemical moiety is replaced with a second chemical moiety. The second chemical moiety can be any desired substituent that does not adversely affect the desired activity of the compound. Examples of substituents are those found in the exemplary compounds and embodiments disclosed herein, as well as halogen; alkyl; heteroalkyl; alkenyl; alkynyl; aryl, heteroaryl, hydroxyl; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$;

—OCH$_2$CONH$_2$; —NH$_2$; —SO$_2$NH$_2$; —OCHF$_2$; —CF$_3$; —OCF$_3$; —NH(alkyl); —N(alkyl)$_2$; —NH(aryl); —N(alkyl)(aryl); —N(aryl)$_2$; —CHO; —CO(alkyl); —CO(aryl); —CO$_2$(alkyl); and —CO$_2$(aryl); and such moieties can also be optionally substituted by a fused-ring structure or bridge, for example —OCH$_2$O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Pharmaceutically acceptable salt" includes, but is not limited to, salts of acidic or basic groups that may be present in the compounds of the invention. Compounds of the invention that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds of the invention that include an amino group also can form pharmaceutically acceptable salts with various amino acids, in addition to the acids mentioned above. Compounds of the invention that are acidic in nature are capable of forming base salts with various pharmacologically acceptable cations. Non-limiting examples of such salts include alkali metal or alkaline earth metal salts and, particularly, calcium, magnesium, sodium, lithium, zinc, potassium, and iron salts.

"Stereoisomer" encompasses all enantiomerically/stereomerically pure and enantiomerically/stereomerically enriched compounds disclosed herein.

"stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90% or 95% or more of one stereoisomer and 20%, 10% or 5% or less of the counter stereoisomer. In some cases, a compound of the invention is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center and more preferably 95% ee with respect to a particular chiral center.

"Stereomerically enriched" or "enantiomerically enriched" encompasses racemic mixtures as well as other mixtures of stereoisomers of compounds of this invention (e.g., R/S=30/70, 35/65, 40/60, 45/55, 55/45, 60/40, 65/35 and 70/30).

"Hydrate" means a compound of the present invention or a salt thereof, that further includes a stoichiometric or non-stoichiometeric amount of water bound by non-covalent intermolecular forces.

"Solvate" means a solvate formed from the association of one or more solvent molecules to a compound of the present invention. The term "solvate" includes hydrates (e.g., monohydrate, dihydrate, trihydrate, tetrahydrate, and the like).

"Polymorph" means solid crystalline forms of a compound of the present invention or complex thereof. Different polymorphs of the same compound can exhibit different physical, chemical and/or spectroscopic properties.

DETAILED DESCRIPTION

Provided herein are self-assembling compounds, that can form ion channels in lipid bilayers or cell membranes, represented by formula (I):

$$(X-H_{DA})_n Y \qquad (I)$$

wherein X is an unsubstituted or substituted hydrocarbyl or heterocyclyl;

n is an integer from 1 to 6;

Y is a monovalent, divalent, trivalent, tetravalent, pentavalent or hexavalent linking group formed by removing one, two, three, four, five and six hydrogen atoms respectively from an unsubstituted or substituted hydrocarbon, carbocycle or heterocycle; and $H_{DA}$ is a divalent group having formula (II):

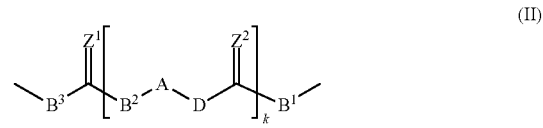

(II)

wherein each of $Z^1$ and $Z^2$ is independently O, S or NR$^1$;

each of A, B$^1$, B$^2$, B$^3$ and D is independently a bond, O, S, NR$^2$ or a substituted or unsubstituted C$_{1-10}$ alkylene; and k is an integer from 1 to 20, where each of R$^1$ and R$^2$ is independently H, acyl, hydrocarbyl, carbocyclyl or heterocyclyl and at least one of B$^1$ and B$^2$ is NH.

In some embodiments, $H_{DA}$ is a substituted hydrocarbylene comprising at least one hydrogen bond donor and at least one hydrogen bond acceptor. In further embodiments, the hydrogen bond donor comprises a hydrogen atom bonded directly to oxygen, nitrogen or sulfur. In further embodiments, the hydrogen bond acceptor is an oxygen, nitrogen, sulfur, fluorine, chlorine, or bromine atom. In certain embodiments, $H_{DA}$ of formula (I) comprises at least one primary amide or secondary amide group.

In certain embodiments, n of formula (I) is 1. In other embodiments, n of formula (I) is 2, and the two X—H$_{DA}$ units are either the same or different.

In some embodiments, X is a hydrocarbyl group such as alkyl, aryl, or aralkyl containing up to 18 carbon atoms, optionally substituted with an oxygen, nitrogen or sulfur containing moiety. In other embodiments, X is heterocyclo moiety optionally substituted with an oxygen, nitrogen or sulfur containing moiety. In one embodiment, $H_{DA}$ contains a diamide and X is a isobutyl group (—CH$_2$CH(CH$_3$)$_2$) linked to $H_{DA}$ unit through a nitrogen atom, forming a terminal isobutylamide. In other embodiments, X of formula (I) is hydrocarbyl or substituted hydrocarbyl. In certain embodiments, X of formula (I) is hydrocarbyl or substituted hydrocarbyl comprising 1 to 14 carbon atoms. In further embodiments, X of formula (I) is alkyl or substituted alkyl having 1 to 14 carbon atoms. In further embodiments, X of formula (I) is isobutyl.

In certain embodiments, Y of formula (I) is a divalent or trivalent linking group formed by removing two or three hydrogen atoms respectively from an unsubstituted or substituted alkane, alkene or alkyne. In further embodiments, Y is a divalent or trivalent linking group formed by removing two or three hydrogen atoms respectively from an unsubstituted or substituted $C_{2-12}$ alkane, alkene or alkyne. In still further embodiments, Y is unsubstituted or substituted propylene or propenylene.

In some embodiments, Y of formula (I) is a divalent or trivalent linking group formed by removing two or three hydrogen atoms respectively from an unsubstituted or substituted monocyclic, bicyclic or tricyclic aromatic carbocycle. In further embodiments, the aromatic carbocycle is an unsubstituted or substituted benzene. In further embodiments, Y is a divalent or trivalent linking group formed by removing two or three hydrogen atoms respectively from unsubstituted benzene.

In some embodiments, Y of formula (I) is a divalent or trivalent linking group formed by removing two or three hydrogen atoms respectively from an unsubstituted or substituted monocyclic, bicyclic or tricyclic heterocycle. In further embodiments, the heterocycle is an unsubstituted or substituted pyridine. In further embodiments, Y is pyridylene.

In certain embodiments, Y of formula (I) is arylene or heteroarylene and each $H_{DA}$ is bonded to a ring atom of Y. In some embodiments, Y of formula (I) is monocyclic, bicyclic or tricyclic arylene. In other embodiments, Y of formula (I) is arylene or heteroarylene having only one 5-, 6-, or 7-membered ring; and each $H_{DA}$ is bonded to a ring atom of Y. In certain embodiments, Y of formula (I) is phenylene, pyridylene, substituted phenylene or substituted pyridylene.

In further embodiments, Y is arylene or heteroarylene; each $H_{DA}$ is bonded to a ring atom of Y; and each X is an unsubstituted or substituted hydrocarbyl having 1 to 14 carbon atoms.

In certain embodiments, $H_{DA}$ may be selected from a variety of organic units containing both hydrogen bond donors and hydrogen bond acceptors. For example, $H_{DA}$ may be substituted hydrocarbyl or heterocyclyl. Without being bound by any theory, it appears that the driving force for self-assembly of compounds to form an ion channel is contributed primarily by a large number of well-defined intermolecularly hydrogen-bonding interactions, which are favoured in the low-dielectric-constant medium of lipid bilayers. In certain embodiments, $H_{DA}$ will be substituted hydrocarbyl, having lower alkyl ether, ester, thioester, amide, hydroxyl, thiol, amino, azo, or halo substituents or other hydrogen bond donors and hydrogen bond acceptors. In one embodiment, for example, $H_{DA}$ contains two amide bonds, such as carboxamide bonds. In another embodiment, $H_{DA}$ is a peptide.

In other embodiments, the self-assembling efficiency of the compounds to form an ion channel may be enhanced when Y links the same or different X—$H_{DA}$ units together, allowing higher possibility for the formation of three-dimensionally intermolecular hydrogen bonding network. In these embodiments, the unit, Y, is in certain embodiments rigid enough to hold the X—$H_{DA}$ units at certain directions in which the compounds may self-assemble more effectively. Y units satisfying these design considerations may be selected from a variety of organic units. In general, these units are carbocyclic or heterocyclic. Non-cyclic Y units are also contemplated. For example, Y may be a 5- or 6-membered ring comprising carbon and optionally a nitrogen, oxygen, or sulfur ring atom wherein the X—$H_{DA}$ units are covalently linked to ring atoms. In one embodiment, Y is a phenylene ring.

The compounds provided herein may be made by one skilled in organic synthesis by known techniques as well as by the general synthetic procedures disclosed herein. The design, synthesis, and characterization of the compounds are described in detail in Examples. In one embodiment, for example, $H_{DA}$ is a peptide and therefore it can be linked with X and Y units through amide bonds, respectively, by using standard peptide coupling methods.

In other embodiments, $H_{DA}$ of formula (I) is represented by formula (III):

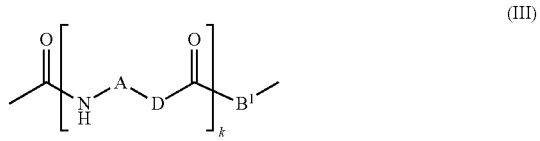

(III)

wherein k is 1 or 2;

A is a bond, O, S, $NR^2$ or a substituted or unsubstituted $C_{1-10}$ alkylene where $R^2$ is H, acyl, hydrocarbyl, carbocyclyl or heterocyclyl;

$B^1$ is O or NH; and

D is $C_{1-3}$ alkylene or $C_{1-3}$ alkylene substituted with one or more hydrocarbyl or heterocyclyl.

In certain embodiments, $H_{DA}$ of formula (I) is represented by formula (IV):

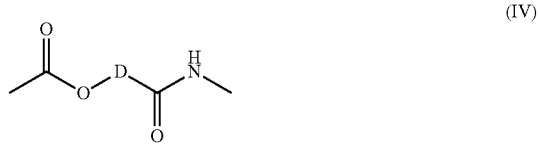

(IV)

wherein D is $C_{1-3}$ alkylene or $C_{1-3}$ alkylene substituted with one or more hydrocarbyl or heterocyclyl.

In other embodiments, $H_{DA}$ of formula (I) is represented by formula (IVB):

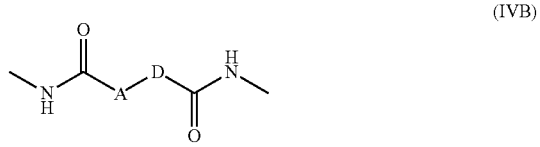

(IVB)

A is a bond, O, S, $NR^2$ or a substituted or unsubstituted $C_{1-10}$ alkylene where $R^2$ is H, acyl, hydrocarbyl, carbocyclyl or heterocyclyl; and D is $C_{1-3}$ alkylene or $C_{1-3}$ alkylene substituted with one or more hydrocarbyl or heterocyclyl.

In certain embodiments, D of formula (III) or (IV) is $C_{1-3}$ alkylene substituted with at least an alkyl, aryl, substituted alkyl or substituted aryl group. In further embodiments, D of formula (III) or (IV) is $C_{1-3}$ alkylene substituted with at least an isobutyl group. In further embodiments, A of formula (III) is a bond; D is methylene or substituted methylene; and k is 1. In further embodiments, A of formula (III) is O; D is methylene or substituted methylene; and k is 1.

In some embodiments, the self-assembling compound has one of the following formulae:
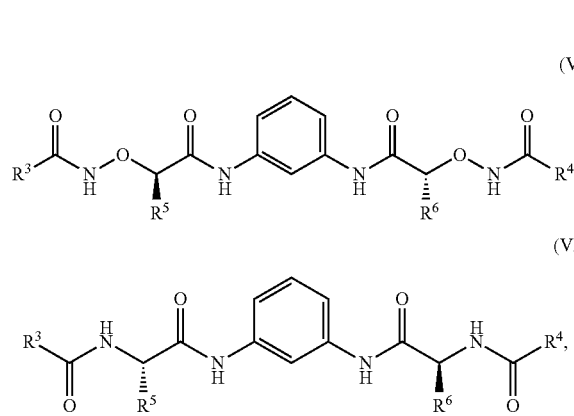
(V)
(VI)
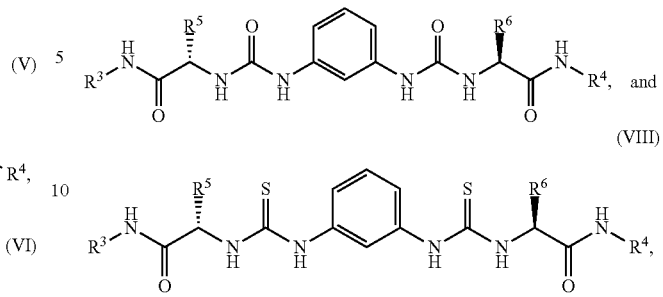
(VII)
(VIII)
wherein each of $R^3$, $R^4$, $R^5$ and $R^6$ is independently H, acyl, hydrocarbyl, carbocyclyl or heterocyclyl.
In certain embodiments, the self-assembling compound is one of the following compounds:
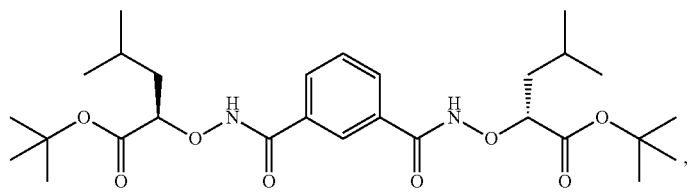
(Example 1)
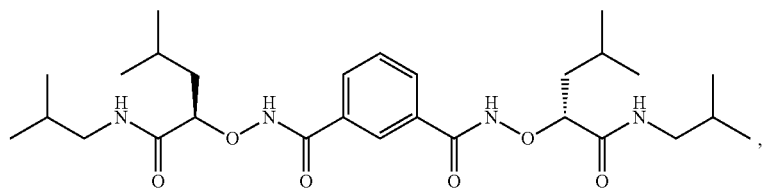
(Example 2)
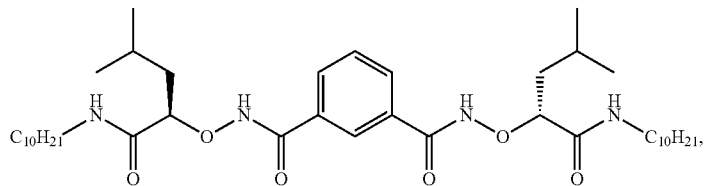
(Example 3)
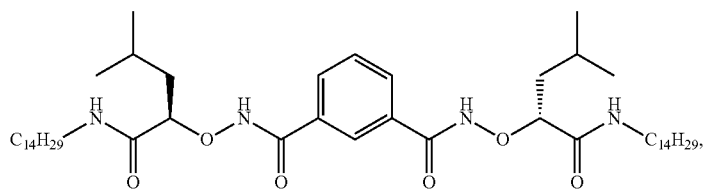
(Example 4)
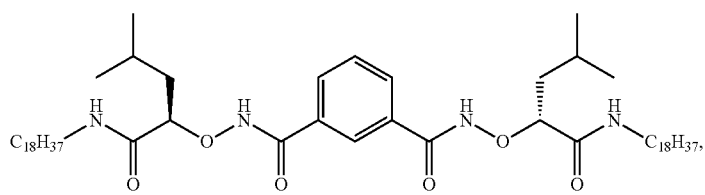
(Example 5)

-continued
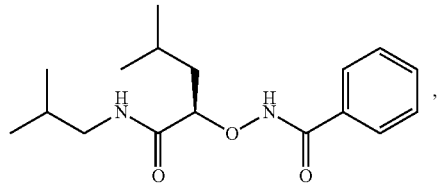
(Example 6)
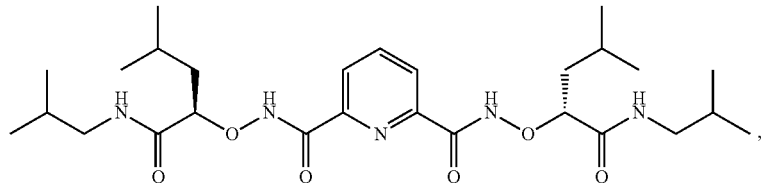
(Example 7)
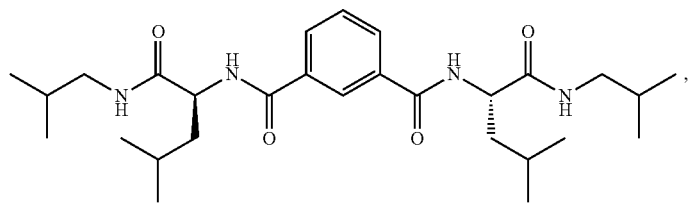
(Example 8)
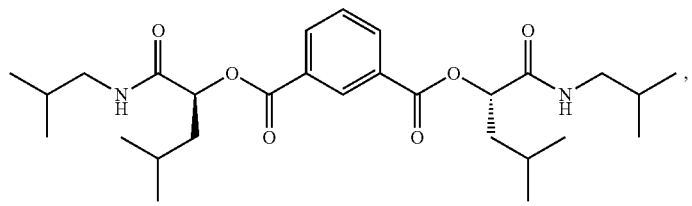
(Example 9)
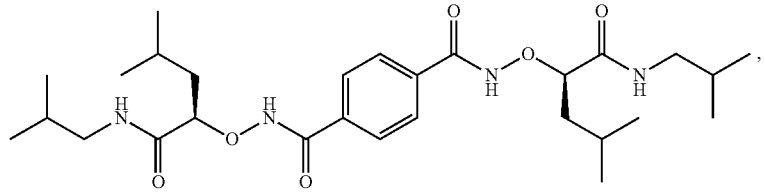
(Example 10)
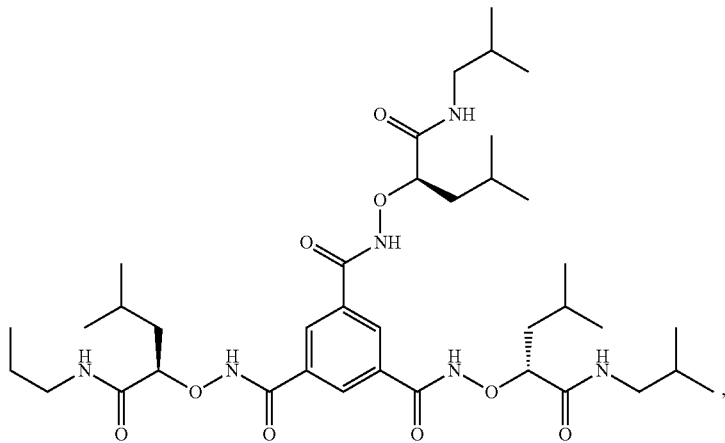
(Example 11)

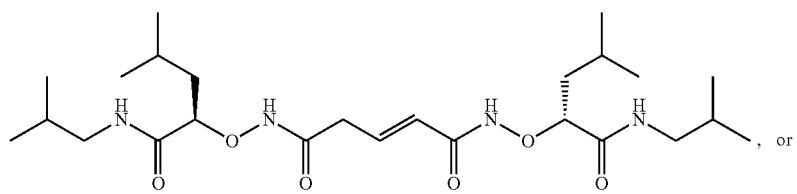

(Example 12)

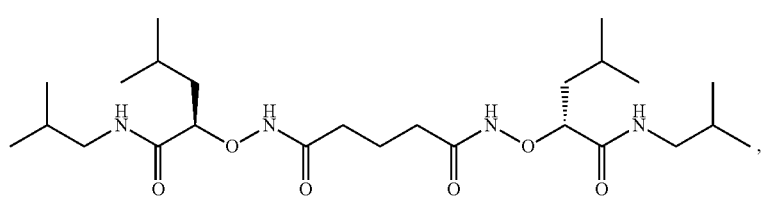

(Example 13)

or a salt, solvate, polymorph or stereoisomer thereof

Synthetic ion channels can be prepared by constructing pore-like structures across the cell membranes. Synthetic ion channels can be classified based on their structures or "designs." Referring to FIG. 1, the simplest design of synthetic ion channels comprises a macromolecule of about 25-40 Å in length having a "unimolecular" pore-like structure. Other design strategies for preparing supramolecular assembly ion channels include the self-assembly of linear, stave-like monomers into a "barrel-stave" pore-like structure; and the stacking of macrocyclic, hoop-like monomers into a "barrel-hoop" pore-like structure. Some smaller macromolecules may self-assemble into a complex barrel-rosette' pore-like structure which can be conceivable either as the "barrel-stave" pore-like structure with fragmented staves or "barrel-hoop" pore-like structure with fragmented hoops.

Figure 2:
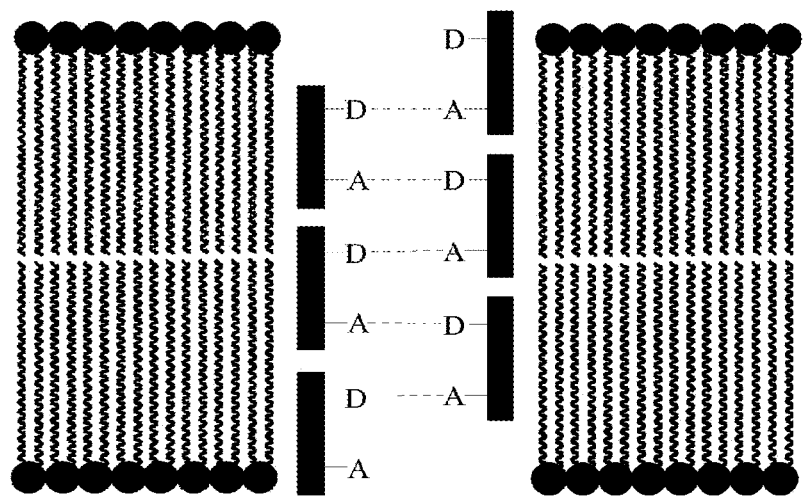
FIG. 2 depicts a synthetic ion channel across a lipid bilayer where the dashed lines represent hydrogen bonds and the thick solid lines represent self-assembling molecules, each of which comprises at least a hydrogen bond donor (represented by D) and at least a hydrogen bond acceptor (represented by A).
Figure 3:
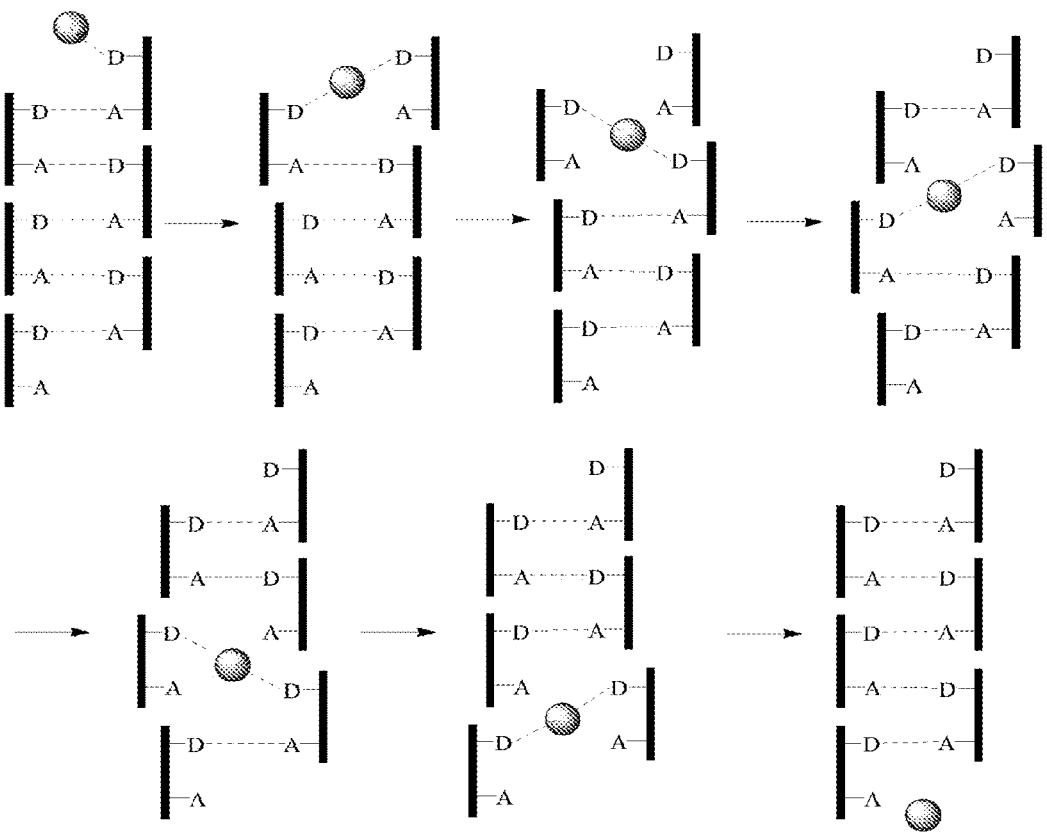
FIG. 3 depicts a possible anion transport process in the synthetic ion channel of FIG. 2 where the sphere represents an anion, the dashed lines represent hydrogen bonds and the thick solid lines represent self-assembling molecules, each of which comprises at least a hydrogen bond donor (represented by D) and at least a hydrogen bond acceptor (represented by A). The anion forms a hydrogen bond individually and sequentially with each of the hydrogen bond donors along the synthetic ion channel when it passes through the channel.
Figure 4:
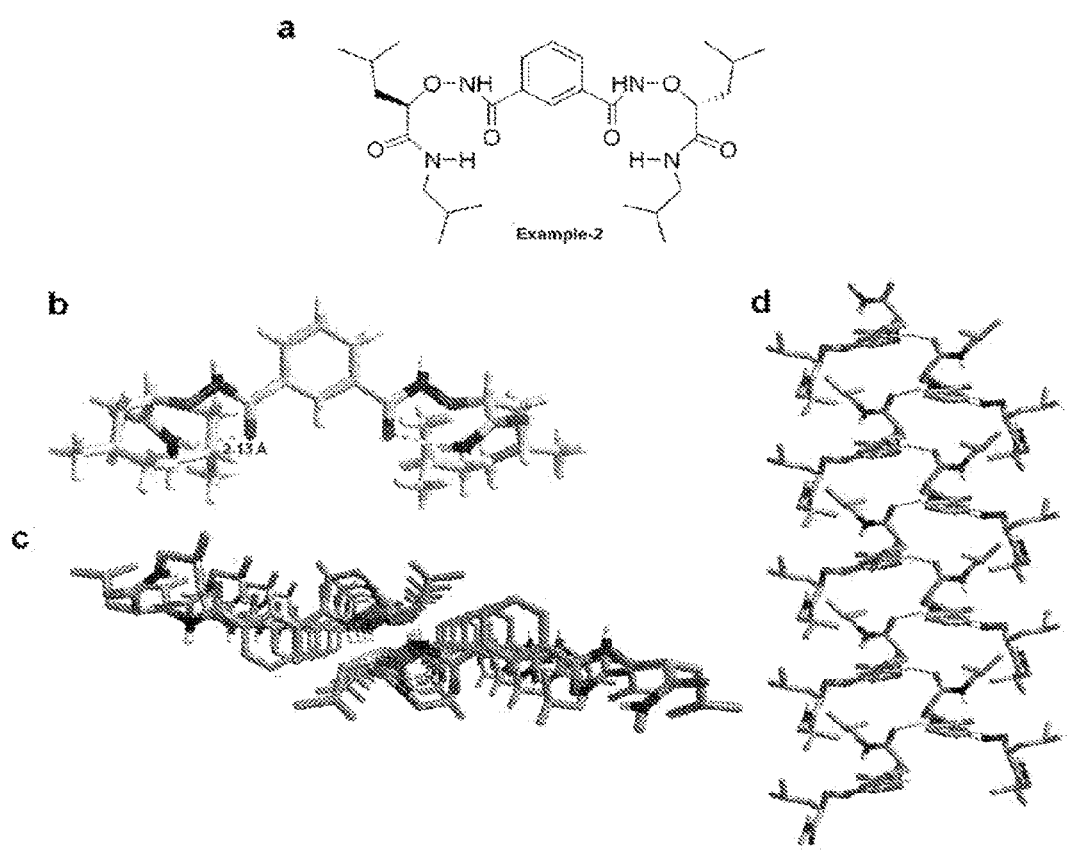
FIG. 4a-d depict various chemical representations Example 2.

Up to now, all of the synthetic ion channels are designed as pore-like structures through which ions transport across the membranes. Provided herein is a new strategy for the design of self-assembling compounds, the molecules of which can self-assemble into ion channels. In some embodiments, the designed molecules can self-assemble through non-covalent interactions to form molecular columns in the transverse direction of lipid membranes. In one embodiment, between two parallel molecular columns, there are intermolecular hydrogen bonds in the lateral direction of the lipid membranes as shown in FIG. 2. When an anion or cation reaches membranes, these intermolecular hydrogen bonds can be reorganized. The donors or acceptors of the original intermolecular hydrogen bonds will afford successive binding sites for stabilization of the anion or the cation, respectively, when they transport across hydrophobic regions of lipid membranes as shown in FIG. 3. In one embodiment, the designed self-assembling compound shows its self-assembled structure in the solid state as shown in FIG. 4b-d having channels that can be used as chloride ion channels.

Without being bound by any theory, although the detailed mechanism is not yet known clearly, the self-assembling compounds disclosed herein have ability to partition into a lipid bilayer and therein self-assemble into an ion channel. These compounds are thought to assemble through well-defined intermolecularly hydrogen-bonding interactions, which are favored in the low-dielectric-constant medium of lipid bilayers. Such a hydrogen bonding induced assembly of compounds with a relatively lipophilic surface, which allows for stable integration and self-assembly in the non-polar environment of lipid bilayers, may penetrate the hydrophobic region of lipid bilayer membranes to form an ion channel.

Physiologically active anions, such as chloride ions, are involved in a number of biological processes. In nature, the transport of chloride ions through cell membranes is regulated by neutral anion binding proteins (chloride ion channels). The self-assembling compounds disclosed herein may partition into lipid bilayers of biological and synthetic cell membranes and function as synthetic ion channels. For example, the compound disclosed in Example 2 can be used to prepare such a synthetic chloride channel. Example 2 can insert into lipid bilayers of liposomes and self-assemble to form a 54 pS (pico-Siemens) chloride channel which shows chloride selectivity and voltage dependent gating. The compound of Example 2 can also efficiently form chloride channels in the membranes of human embryonic kidney (HEK 293) cells and thereby dramatically increases cell chloride currents at a remarkably low concentration of 50 nM (nanomolar). The ion channel behavior of the compound of Example 2 demonstrates that the synthetic ion channel structures disclosed herein can afford selective membrane permeability equivalent in many respects to that observed in natural protein channels.

The self-assembling compounds disclosed herein may modulate the concentration of a target anion to allow study on the behavior of physiological systems or models thereof. Alternatively, anion concentration may be varied or regulated by application of the self-assembling compounds in therapeutic systems, to increase or decrease anion concentrations in order to counteract or otherwise modify diseased or unwanted conditions. Accordingly, the self-assembling compounds disclosed herein may be used to modulate the influx or efflux of anions, including, but not limited to halides such as chloride and bromide, or other anions such as nitrate and bicarbonate, into a mammalian cell or other membrane systems, such as, mitochondria, endosomes, lysosomes, secretory vesicles, endoplasmic reticula, nucleii, Golgi apparatus, intracellular transport vesicles, MHC processing vesicles, reconstituted ruffled membrane vesicles from osteoclasts, and others having a lipid bilayer membrane.

In biological and synthetic systems, the composition of a cell membrane varies depending upon its location in a biological system and its desired function in synthetic systems. Therefore, provided is the formation of synthetic ion channels in a membrane irrespective of whether the membrane is of natural or synthetic origin. In certain embodiments, the self-assembling compounds disclosed herein have the ability to self-assemble through hydrogen bonds in physiological and non-physiological systems and form anion channels in lipid bilayers or cell membranes.

Also provided is a method of treating, preventing or ameliorating symptoms of a disease or condition associated with a cellular chloride imbalance using the compounds and compositions provided herein. Non-limiting examples of such a disease or condition include cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy and osteopetrose. In some embodiments, the self-assembling compounds disclosed herein are inserted into the lipid bilayer of a mammalian cell in an appropriate amount, and manner, as determined by characteristics of the particular compound, patient profile, and disease in question.

In certain embodiments, the compounds and compositions may be applied in vivo, to tissues such as the lungs, trachea, skin, muscle, brain, liver, heart, spleen, bone marrow, thymus, bladder, lymph, blood, pancreas, stomach, kidney, ovaries, testicles, rectum, peripheral or central nervous system, eyes, lymphoid organs, cartilage and endothelium. In certain embodiments, the target cell is a muscle cell (such as a skeleton muscle cell, a cardiac muscle cell and a smooth muscle cell), a nerve cell, a hematopoietic stem cell, a neuron cell, an epithelium cell or alternatively a cell of the airways. In other embodiments, the target cell is a tracheal or pulmonary cell. In further embodiments, the target cell is a cell of the respiratory epithelium.

Increasing chloride permeability of apical membranes of pulmonary has been shown to reduce the pathophysiology associated with cystic fibrosis mutations. Therefore, the application of a chloride channel-forming compound herein may permit increased chloride permeability of the apical pulmonary epithelia and thereby compensate for cystic fibrosis mutations.

Cystic fibrosis (CF) is one of the most common fatal genetic diseases in Caucasians. The cystic fibrosis transmembrane conductance regulator (CFTR) is a chloride channel located at the apical membrane of epithelial cells, the activity of which is regulated by phosphorylation and intracellular nucleotides. In airway epithelial cells, the CFTR is the major chloride transport pathway and regulates active ion transport-mediated fluid transport. In CF, mutations in the gene encoding CFTR cause defective transepithelial chloride and fluid transport, with resultant impairment of airway mucociliary clearance and reduction of the bactericidal activity of salt-sensitive defensins. It has been proposed that these deficits are responsible for the recurrent infections and subsequent destruction of the lungs in CF patients.

Several therapeutic approaches are being developed concurrently for the treatment of CF. These include (1) using agents that improve the bactericidal activity and viscosity of the mucous fluid lining the airways; (2) using agents that activate alternative chloride channels to compensate for the CFTR chloride channel defect; (3) protein and gene augmentation therapy; and (4) using pharmacological agents that rescue the intracellular trafficking defect associated with the most common mutant form of CFTR or that suppress premature stop mutations. Hence, the development of synthetic anion channels has significant utility in terms of investigating cellular anion imbalances and in modulating such conditions.

The self-assembling compounds disclosed herein can be used as a medicament for curative or preventive purpose. Specifically, the self-assembling compounds may be used in a method of therapeutic treatment that consists of introducing the compound into the lipid bilayer of target cells which are engaged in ion transport. As such, the compounds may be used in the preparation of a medicament for curative or preventive purposes, intended for the treatment of the human or animal body.

The medicament may be administered directly in vivo, for example, into a muscle by infusion, into the lungs by aerosol and the like. It is also possible to adopt an ex vivo approach, which consists of collecting cells from the patient (bone marrow stem cells, peripheral blood lymphocytes, muscle cells, nerve cells, neuron cells, epithelial cells and the like), administering the compounds and re-administering the cells to the patient.

The self-assembling compounds provided herein may be administered by the intramuscular, intratracheal, intranasal, intracerebral, intrapleural, intratumoral, intracardiac, intragastric, intraperitoneal, epidermal, intravenous or intraarterial route by a syringe or by any other equivalent means, systems suitable for the treatment of the airways or of the mucous membranes such as inhalation, instillation or aerosolization. Other routes of administration include application of a cream, oral administration or any other means known to the person skilled in the art and applicable to the compounds and compositions provided herein.

Administration may be achieved by a variety of different routes. One route is oral administration of a composition such as a pill, capsule or suspension. Such composition may be prepared according to any method known in the art, and may comprise any of a variety of inactive ingredients. Suitable excipients for use within such compositions include insert diluents (which may be solid materials, aqueous solutions and/or oils) such as calcium, potassium, or sodium carbonate, lactose, calcium, potassium, or sodium phosphate, water, arachis oil, peanut oil, liquid paraffin or olive oil; granulating and disintegrating agents such as maize starch, gelatin or acacia and/or lubricating agents suchas magnesium stearate, stearic acid, or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth, and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid, polyethylene glycols, polyethylene glycol ethers, and others known to those of ordinary skill in the art.

In other embodiments, provided are methods in which the compounds are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of co-solvents, surfactants, stabilizers (e.g., antioxidants, chelating agents, insert gases and buffers). For compositions to be administered from multiple dose containers, antimicrobial agents are typically added. Such compositions may also be filtered and sterilized, and may be lyophilized to provide enhanced stability and to improve solubility.

Pharmaceutical compositions can be administered in an amount, and with a frequency, that is effective to inhibit or alleviate the symptoms of a disease or condition, such as cystic fibrosis, and/or delay the progression of the disease. The precise dosage and duration of treatment may be determined empirically using known testing protocols or by testing the composition in model systems known in the art and extrapolating therefrom. Dosages may also vary with the severity of the disease. A pharmaceutical composition may be formulated and administered to exert a therapeutically useful effect while minimizing undesirable side effects. It will be apparent that, for any particular subject, specific dosage regimens may be adjusted over time according to the individual need.

As noted above, a pharmaceutical composition may be administered to a mammal to stimulate chloride transport, or to treat, manage or prevent cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy or osteopetrose. Patients that may benefit from administration of a self-assembling compound provided herein are those afflicted with cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy or osteopetrose. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport as provided herein.

Also provided are methods of administering the pharmaceutical compositions by intravenous, oral, instillation, inhalation, topical, intraperitoneal, subcutaneous, or intramuscular routes. The pharmaceutical compositions may be administered, for example, in the form of capsules, powders, tablets, liquids, solutions, and aerosolized solutions. Also provided are methods of treating diseases or other conditions in a mammal that give rise to defective anion transport across cell membranes.

Additional features and advantages of the invention will be set forth, and in part will be apparent from the description, or may be learned by practice of the invention.

Dosages of the compositions provided will vary, depending on factors such as half-life of the compound, potential adverse effects of the compound or of degradation products thereof, the route of administration, the condition of the patient, and the like. Such factors are capable of determination by those skilled in the art. The exact dose level given on a daily basis, of course, is meant to be adapted by a physician to provide the optimum therapeutic response.

EXAMPLES

The following Examples 1-12 are detailed descriptions of the methods of making and using the compounds represented by general formula (I). Other compounds with the scope of this disclosure may be prepared using the procedures with appropriate starting material which are apparent to those of skill in the art. These examples are presented for illustrative purposes only and are not intended to limit the scope of the invention.

Preparation of Example 1

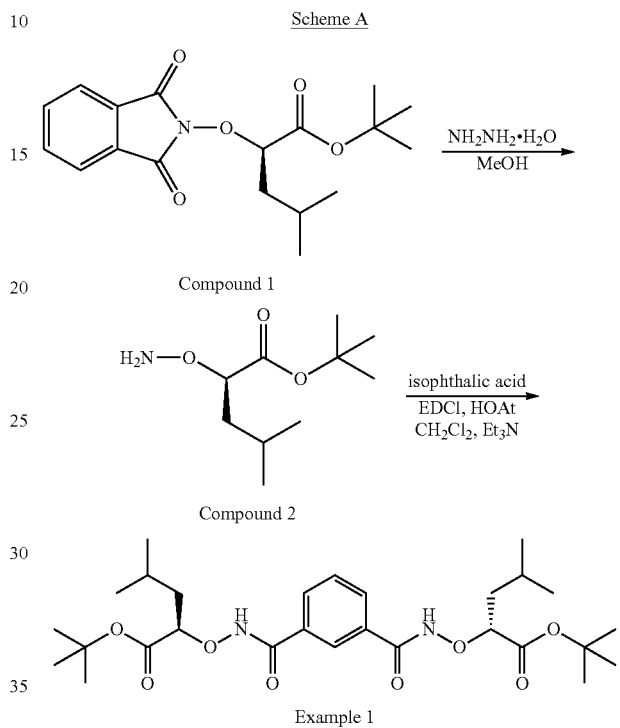

Example 1 was prepared according to Scheme A above. The starting material, D-tert-butyl 2-phthalimidoxy-4-methylpentanoate (Compound 1), was synthesized according to the procedures described in Yang et al., J. Org. Chem, 2001, 66, 7303-7312. Compound 1, a white crystalline solid, was characterized by the following data: m.p. 92-93° C.; $[\alpha]^{20}_D$+ 77.0° (c 1.01, CHCl$_3$); $^1$H NMR (300 MHz, CDCl$_3$) δ 7.85-7.81 (m, 2H), 7.78-7.74 (m, 2H), 4.74 (dd, J=8.5, 5.4 Hz, 1H), 2.05-1.91 (m, 2H), 1.72-1.63 (m, 1H), 1.46 (s, 9H), 1.07 (d, J=6.3 Hz, 3H), 1.00 (d, J=6.3 Hz, 3H); $^{13}$C NMR (75 MHz, CDCl$_3$) δ 169.13, 163.21, 134.50, 128.87, 123.53, 84.74, 83.39, 39.89, 27.82, 24.47, 22.90, 21.96; IR (CHCl$_3$) 3032, 1793, 1738 cm$^{-1}$; LRMS (EI, 70 ev) m/z 333 (M$^+$, 1), 278 (6), 232 (17), 164 (15), 148 (100); HRMS (EI) for C$_{18}$H$_{23}$NO$_5$ (M$^+$): calculated 333.1576. found 333.1573.

To a solution of Compound 1 (2.00 g, 6.0 mmol) in CH$_3$OH (20 mL) was added NH$_2$NH$_2$·H$_2$O (900 mg, 18.0 mmol). A white precipitate appeared after 1 hour. After being stirred at room temperature for 2.5 hours, the reaction mixture was concentrated under vacuo. The residue was dissolved in CH$_2$Cl$_2$ and washed with 5% NaHCO$_3$ twice and then with brine. The organic layer was dried over anhydrous Na$_2$SO$_4$ and concentrated to provide a mixture of the free amine (Compound 2) and phthahydroazide as a colorless oil. This mixture was immediately used in the peptide coupling reaction below without further purification.

Peptide Coupling Reaction.

Freshly distilled $CH_2Cl_2$ (80 mL) was added to a flask containing dried Compound 2 under nitrogen atmosphere, followed by the additions of 1-hydroxy-7-azabenzotriazole (HOAt, 2.11 g, 15.6 mmol), isophthalic acid (498 mg, 3.0 mmol), triethylamine (0.83 mL, 6.0 mmol), and finally 1-ethyl-3-(3-dimethylamino-propyl)-carbodiimide (EDCI, 5.35 g, 18.0 mmol). After stirred overnight, the reaction mixture was diluted with $CH_2Cl_2$. The organic layer was washed with 5% $NaHCO_3$ and brine, then dried over anhydrous $MgSO_4$ and concentrated. The crude oil was purified by flash column chromatography to afford 1.32 g (82% yield) of Example 1 as white solid. Example 1 was characterized by the following data: m.p. 57-59° C.; $[\alpha]^{20}{}_D$+78.1° (c 0.50, $CHCl_3$); $^1H$ NMR (300 MHz, $CDCl_3$) δ 9.86 (br, 2H), 8.14 (t, J=1.5 Hz, 1H), 7.90 (dd, J=7.8, 1.5 Hz, 2H), 7.48 (t, J=7.8 Hz, 1H), 4.53 (dd, J=9.0, 4.2 Hz, 2H), 2.01-1.92 (m, 2H), 1.77-1.68 (m, 2H), 1.60-1.51 (m, 2H), 1.46 (s, 18H), 1.02 (d, J=6.5 Hz, 12H), 0.96 (d, J=6.5 Hz, 6H); $^{13}C$ NMR (75 MHz, $CDCl_3$) δ 171.80, 164.58, 132.18, 130.41, 128.91, 125.58, 82.37, 82.17, 39.86, 27.97, 24.60, 23.18, 23.01, 21.79; IR ($CHCl_3$) 3403, 3019, 1730, 1688 $cm^{-1}$; LRMS (EI, 20 eV) m/z 536 ($M^+$); HRMS (EI 20 eV) for $C_{28}H_{44}N_2O_8$ ($M^+$) calculated 536.3098. found 536.3078.

Preparation of Example 2 mL) through a syringe at room temperature. After being stirred at room temperature for 3 hour, the reaction mixture was concentrated under vacuo. The residue was azeotroped with toluene twice to give free acid Compound 3 as a white solid and the white solid was used directly in the peptide coupling.

Freshly distilled $CH_2Cl_2$ (50 mL) was added to a flask containing dried free acid Compound 3 under nitrogen atmosphere, followed by the addition of HOAt (354 mg, 2.6 mmol), isobutylamine (0.21 mL, 2.1 mmol), and finally EDCI (891 mg, 3.0 mmol). After stirred overnight, the reaction mixture was diluted with $CH_2Cl_2$. The organic layer was washed with 5% $NaHCO_3$ and brine, then dried over anhydrous $MgSO_4$ and concentrated. The crude oil was purified by flash column chromatography to afford 492 mg of Example 2 (92% yield) as a white solid. Example 2 was characterized by the following data: m.p. 176-178° C.; $[\alpha]^{20}{}_D$+67.3° (c 0.50, $CHCl_3$); $^1H$ NMR (600 MHz, $CDCl_3$) δ 10.43 (s, 2H), 8.12 (s, 1H), 8.07 (t, J=5.7 Hz, 2H), 8.04 (d, J=7.8 Hz, 2H), 7.57 (t, J=7.8 Hz, 1H), 4.40 (dd, J=9.5, 3.4 Hz, 2H), 3.05-3.01 (m, 2H), 2.91-2.88 (m, 2H), 1.86-1.62 (m, 8H), 0.92 (d, J=6.6 Hz, 12H), 0.84 (d, J=6.7 Hz, 6H), 0.78 (d, J=6.7 Hz, 6H); $^{13}C$ NMR (75 MHz, $CDCl_3$) δ 171.89, 166.14, 131.97, 131.30, 129.69, 124.93, 85.60, 46.69, 41.15, 28.29, 24.85, 23.18, Scheme B

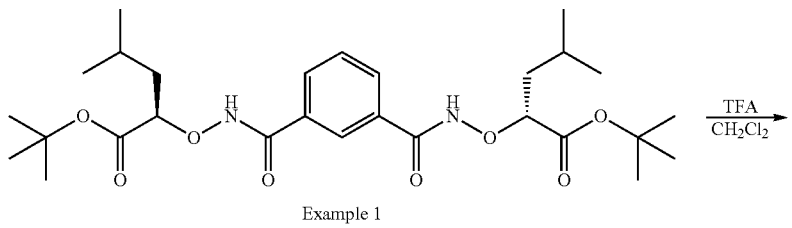

Example 1

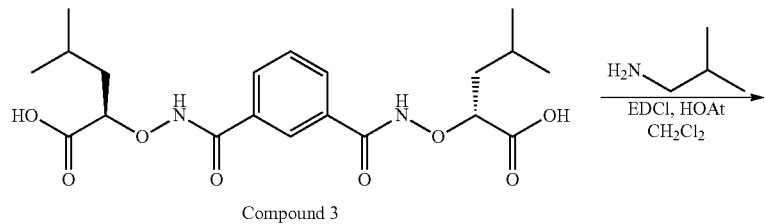

Compound 3

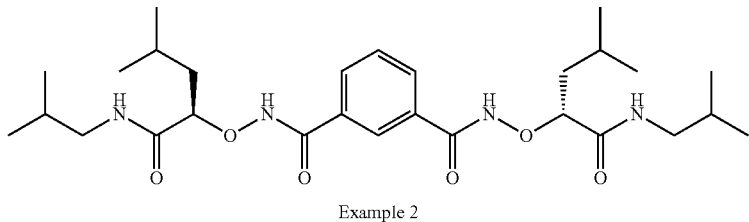

Example 2

Example 2 was prepared according to Scheme B above. To the solution of Example 1 (537 mg, 1.0 mmol) in $CH_2Cl_2$ (5 mL) was carefully added an equal volume of $CF_3COOH$ (5 21.81, 20.04, 19.99; IR ($CHCl_3$) 3332, 3185, 1663 $cm^{-1}$; LRMS (EI, 20 eV) m/z 534 ($M^+$); HRMS (EI, 20 eV) for $C_{28}H_{46}N_4O_6$ ($M^+$): calculated 534.3417. found 534.3435.

Preparation of Example 3

Scheme C

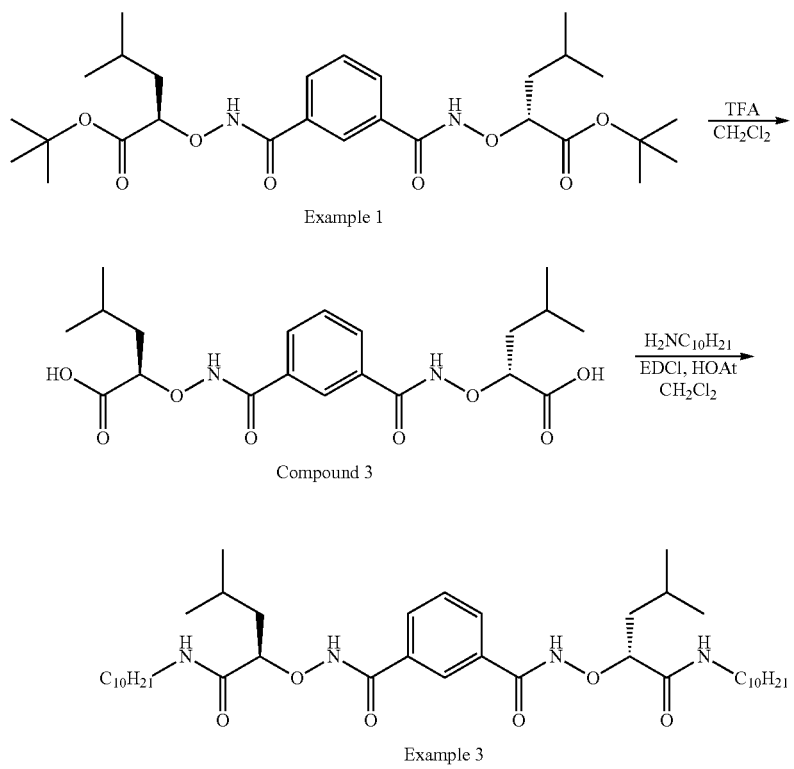

Example 3 was prepared according to Scheme C above which was similar to Scheme B for Example 2 except that isobutylamine was replaced with decylamine. Example 3 was isolated as a colorless oil. Example 3 was characterized by the following data: $[\alpha]^{20}_D$ +34.5° (c 1.00, CHCl$_3$); $^1$H NMR (400 MHz, CDCl$_3$) δ 11.32 (s, 2H), 8.28 (br, 2H), 8.19 (s, 1H), 8.05 (d, J=7.5 Hz, 2H), 7.52 (t, J=7.5 Hz, 1H), 4.38 (br, 2H), 3.13-3.02 (m, 4H), 1.82 (m, 2H), 1.65-1.55 (m, 4H), 1.42 (br, 4H), 1.35-1.25 (m, 28H), 0.89-0.85 (m, 18H); $^{13}$C NMR (100 MHz, CDCl$_3$) δ 172.30, 165.91, 132.05, 131.29, 129.37, 124.98, 85.31, 41.17, 39.47, 31.89, 29.55, 29.53, 29.30, 29.12, 26.91, 24.73, 23.18, 22.67, 21.79, 14.10; IR (CHCl$_3$) 3446, 1662 cm$^{-1}$; LRMS (FAB) m/z 704 (M$^+$, 1); HRMS (FAB) for C$_{40}$H$_{71}$N$_4$O$_6$ (M$^+$, 1): calculated 703.5374. found 703.5354.

Preparation of Example 4

Scheme D

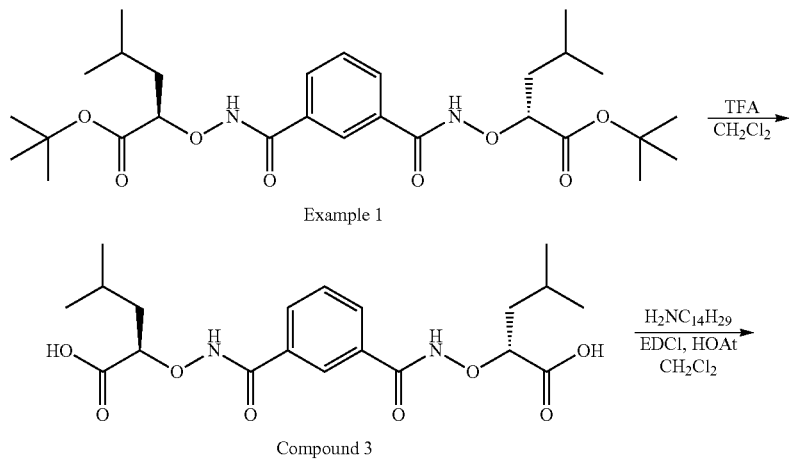

-continued

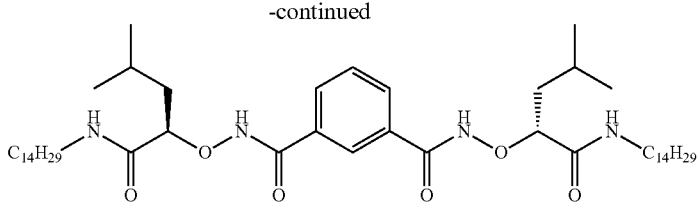

Example 4

Example 4 was prepared according to Scheme D above which was similar to Scheme B for Example 2 except that isobutylamine was replaced with tetradecylamine. Example 4 was isolated as a yellow oil. Example 4 was characterized by the following data: $[\alpha]^{20}_D$+52.2° (c 1.00, CHCl$_3$); $^1$H NMR (400 MHz, CDCl$_3$) δ 10.97 (s, 2H), 8.15 (br, 3H), 8.05 (d, J=7.8 Hz, 2H), 7.53 (t, J=7.8 Hz, 1H), 4.36 (dd, J=9.1, 3.7 Hz, 2H), 3.16-3.06 (m, 4H), 1.80 (m, 2H), 1.65-1.55 (m, 4H), 1.43 (br, 4H), 1.25-1.17 (m, 44H), 0.89-0.85 (m, 18H); $^{13}$C NMR (100 MHz, CDCl$_3$) δ 171.96, 165.92, 132.00, 131.26, 129.43, 124.93, 85.38, 41.07, 39.39, 31.89, 29.67, 29.64, 29.59, 29.53, 29.33, 29.27, 29.14, 26.89, 24.72, 23.12, 22.66, 21.77, 14.08; IR (CHCl$_3$) 3441, 3342, 1662 cm$^{-1}$; LRMS (FAB) m/z 816 (M$^+$, 1): HRMS (FAB) for C$_{43}$H$_{87}$N$_4$O$_6$ calculated 815.6626. found 815.6610.

Preparation of Example 5

Example 5 was prepared according to Scheme E above which was similar to Scheme B for Example 2 except that isobutylamine was replaced with octadecylamine. Example 5 was isolated as a white solid. Example 5 was characterized by the following data: m.p. 88-90° C.; $[\alpha]^{70}_D$+43.9° (c 1.00, CHCl$_3$); $^1$H NMR (300 MHz, CDCl$_3$) δ 11.11 (s, 2H), 8.18 (br, 3H), 8.05 (d, J=7.7 Hz, 2H), 7.55 (t, J=7.7 Hz, 1H), 4.36 (dd, J=8.8, 3.4 Hz, 2H), 3.15-3.05 (m, 4H), 1.80 (m, 2H), 1.65-1.54 (m, 4H), 1.41 (br, 4H), 1.30-1.16 (m, 60H), 0.89-0.84 (m, 18H); $^{13}$C NMR (75 MHz, CDCl$_3$) δ 172.03, 165.89, 131.98, 129.37, 124.98, 85.31, 41.06, 39.39, 31.89, 29.69, 29.60, 29.53, 29.33, 29.28, 29.12, 26.88, 24.68, 23.12, 22.56, 21.74, 14.08; IR (CHCl$_3$) 3444, 3345, 1662 cm$^{-1}$; LRMS (FAB) m/z 928 (M$^-$1); HRMS (MALDI) for C$_{56}$H$_{102}$N$_4$O$_6$ (M$^+$+Na): calculated 927.4323. found 949.7678.

Scheme E

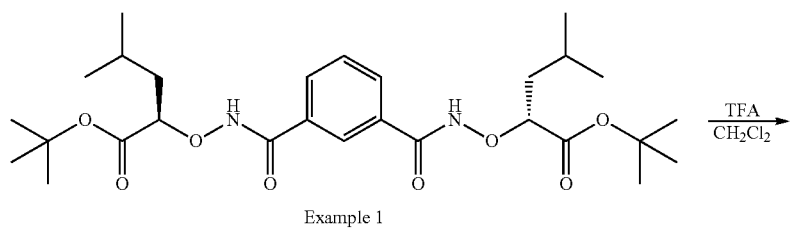

Example 1

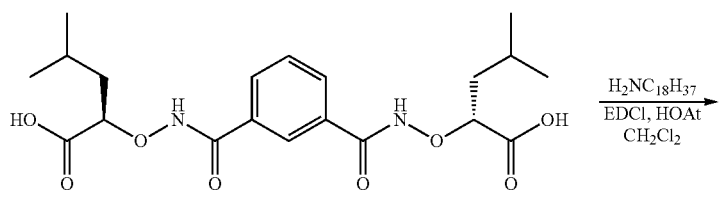

Compound 3

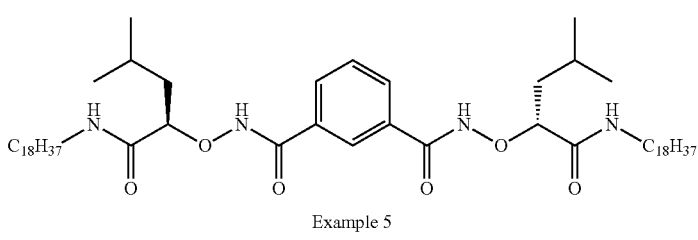

Example 5

Preparation of Example 6

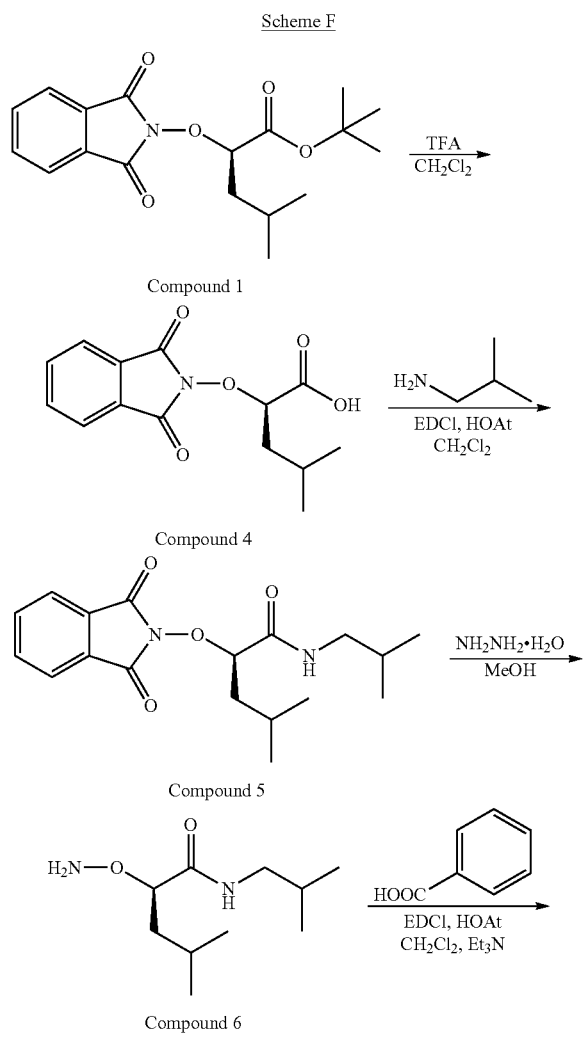

Example 6 was prepared according to Scheme F above. To a solution of Compound 1 (1.00 g, 3.0 mmol) in CH$_2$Cl$_2$ (10 mL) was carefully added equal volume of CF$_3$COOH (10 mL) through a syringe at room temperature. After stirred at room temperature for 3 hours, the reaction mixture was concentrated under vacuo. The residue was azeotroped with toluene twice to give Compound 4 as a white solid and the white solid was used directly in the next step below.

Freshly distilled CH$_2$Cl$_2$ (80 mL) was added to a flask containing dried Compound 4 under nitrogen atmosphere, followed by the addition of HOAt (530 mg, 3.9 mmol), isobutylamine (0.32 mL, 3.15 mmol), and finally EDCI (1.34 g, 4.5 mmol). After being stirred overnight, the reaction mixture was diluted with CH$_2$Cl$_2$. The organic layer was washed with 5% NaHCO$_3$ and brine, then dried over anhydrous MgSO$_4$ and concentrated to afford compound 5 (0.99 g, 99%) as a white solid (Compound 5), which was used directly in the next step without further purification.

To a solution of Compound 5 in CH$_3$OH (10 mL) was added NH$_2$NH$_2$·H$_2$O (450 mg, 9.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (530 mg, 3.9 mmol), benzoic acid (366 mg, 3.0 mmol), triethylamine (0.41 mL, 3.0 mmol), and finally EDCI (1.34 g, 4.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford Example 6 (832 mg, 86%) as a white solid. Example 6 was characterized by the following data: m.p. 130-132° C.; $[\alpha]^{20}_D$ +31.7° (c 1.00, CHCl$_3$); $^1$H NMR (400 MHz, CDCl$_3$) δ 9.98 (br, 1H), 8.21 (br, 1H), 7.75 (d, J=7.5 Hz, 2H), 7.52 (t, J=7.3 Hz, 1H), 7.52 (t, J=7.6 Hz, 2H), 4.40 (dd, J=9.4, 3.8 Hz, 1H), 3.13-2.97 (m, 2H), 1.85-1.61 (m, 4H), 0.92-0.85 (m, 12H); $^{13}$C NMR (75 MHz, CDCl$_3$) δ 171.94, 167.74, 132.41, 131.01, 128.65, 127.27, 85.40, 46.61, 40.97, 28.32, 24.71, 23.19, 21.62, 20.06, 19.88; IR (CHCl$_3$) 3345, 1659 cm$^{-1}$; LRMS (EI, 20 eV) m/z 307 (M$^+$, 1); HRMS (EI, 20 eV) for C$_{17}$H$_{26}$N$_2$O$_3$(M$^+$): calculated 306.1943. found 306.1923.

Preparation of Example 7

Scheme G

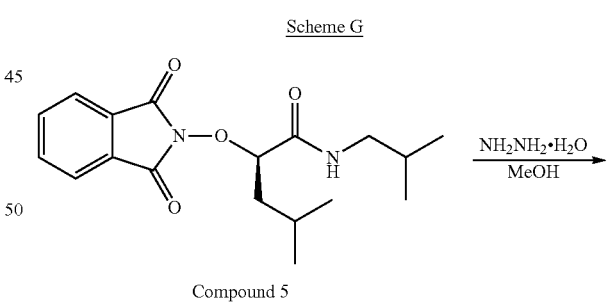

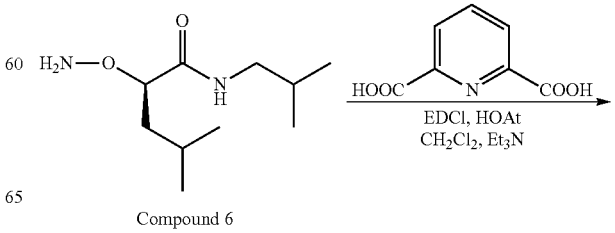

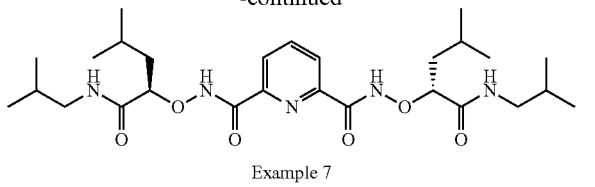

Example 7

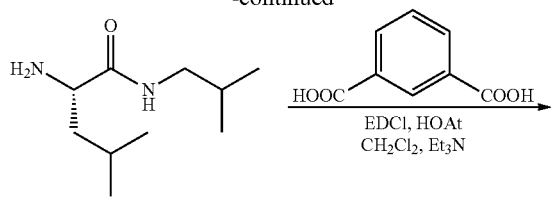

Compound 9

Example 7 was prepared according to Scheme G above. To a solution of Compound 5 (332 mg, 1 mmol) in CH₃OH (10 mL) was added NH₂NH₂.H₂O (150 mg, 3.0 mmol). A white precipitate appeared after 1 hour. After stirred at room temperature for 2.5 hours, the reaction mixture was concentrated under vacuo. The residue was dissolved in CH₂Cl₂ and was washed with 5% NaHCO₃ twice and then with brine. The organic layer was dried over anhydrous Na₂SO₄ and concentrated to provide a mixture of Compound 6 and phthahydroazide as a colorless oil. This mixture was immediately used in the next step without further purification.

Freshly distilled CH₂Cl₂ (50 mL) was added to a flask containing dried Compound 6 under nitrogen atmosphere, followed by the addition of HOAt (177 mg, 1.3 mmol), pyridine-2,6-dicarboxylic acid (366 mg, 0.5 mmol), triethylamine (0.14 mL, 1.0 mmol), and finally EDCI (447 mg, 1.5 mmol). After stirred overnight, the reaction mixture was diluted with CH₂Cl₂. The organic layer was washed with 5% NaHCO₃ and brine, then dried over anhydrous MgSO₄ and concentrated. The crude oil was purified by flash column chromatography to afford Example 7 (214 mg, 80%) as a white solid. Example 7 was characterized by the following data: m.p. 175-177° C.; $[\alpha]^{20}_D$+117.2° (c 0.50, CHCl₃); $^1$H NMR (300 MHz, CDCl₃) δ 11.97 (s, 2H), 8.31 (d, J=7.8 Hz, 2H), 8.20 (t, J=5.7 Hz, 2H), 8.10 (t, J=7.8 Hz, 1H), 4.41 (dd, J=8.6, 4.2 Hz, 2H), 3.05-2.98 (m, 4H), 1.81-1.60 (m, 8H), 0.90-0.78 (m, 24H); $^{13}$C NMR (75 MHz, CDCl₃) δ 171.73, 162.30, 147.51, 139.20, 125.59, 85.30, 46.68, 41.12, 28.16, 24.65, 23.03, 21.97, 19.99, 19.95; IR(CHCl₃) 3321, 1673 cm$^{-1}$; LRMS (EI, 20 eV) m/z 535 (M⁺): HRMS (EI, 20 eV) for C₂₇H₄₅N₅O₆ (M⁺): calculated 535.3370. found 535.3371.

Preparation of Example 8

Scheme H

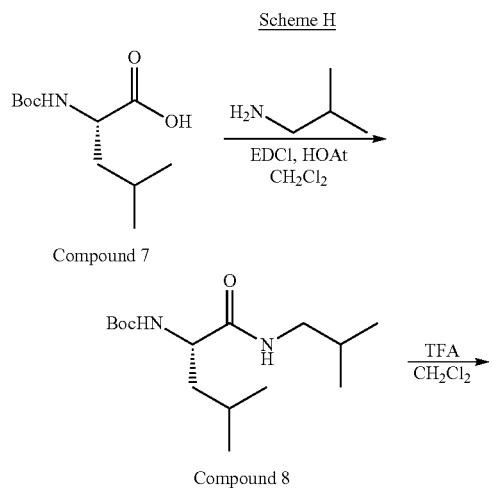

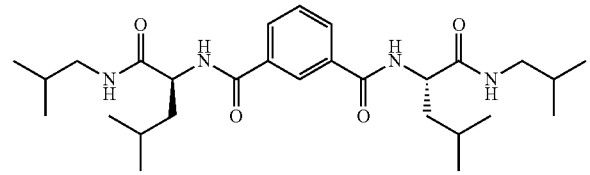

Example 8

Example 8 was prepared according to Scheme H above. N-Boc-L-leucine (Compound 7) (693 mg 3.0 mmol) was dissolved in freshly distilled CH₂Cl₂ (50 mL) under nitrogen atmosphere, followed by the addition of HOAt (530 mg, 3.9 mmol), isobutylamine (0.32 mL, 3.15 mmol), and finally EDCI (1.34 g, 4.5 mmol). After stirred overnight, the reaction mixture was diluted with CH₂Cl₂. The organic layer was washed with 5% NaHCO₃ and brine, then dried over anhydrous MgSO₄ and concentrated to afford Compound 8 (851 mg, 99%) as a white solid, which was used directly in the next step without further purification.

To a solution of Compound 8 in CH₂Cl₂ (5 mL) was carefully added equal volume of CF₃COOH (5 mL) through a syringe at room temperature. After stirred at room temperature for 3 hour, the reaction mixture was concentrated under vacuo. The residue was dissolved in CHCl₃, washed with K₂CO₃ solution (pH=12) and brine, dried over anhydrous Na₂SO₄, and concentrated to give free amine Compound 9 as a colorless oil, which was used directly in the next step.

Freshly distilled CH₂Cl₂ (50 mL) was added to a flask containing dried Compound 9 under nitrogen atmosphere, followed by the addition of HOAt (530 mg, 3.9 mmol), isophthalic acid (249 mg, 1.5 mmol), triethylamine (0.41 mL, 3.0 mmol), and finally EDCI (1.34 g, 4.5 mmol). After being stirred overnight, the reaction mixture was diluted with CH₂Cl₂. The organic layer was washed with 5% NaHCO₃ and brine, then dried over anhydrous MgSO₄ and concentrated. The crude oil was purified by flash column chromatography to afford Example 8 (617 mg, 82%) as a white solid. Example 8 was characterized by the following data: m.p. 240-242° C.; $[\alpha]^{20}_D$32.1° (c, 1.00, CHCl₃); $^1$H NMR (500 MHz, CDCl₃) δ 8.20 (s, 1H), 7.92 (d, J=7.8 Hz 2H), 7.48 (t, J=7.8 Hz, 1H), 7.09 (d, J=8.2 Hz, 2H), 6.35 (t, J=5.8 Hz, 2H), 4.65 (m, 2H), 3.15-3.10 (m, 2H), 3.05-3.00 (m, 2H), 1.81-1.69 (m, 8H), 0.97 (d, J=6.7 Hz, 12H), 0.90 (d, J=6.7 Hz, 12H); $^{13}$C NMR (125 MHz, CDCl₃) δ 172.01, 166.53, 134.19, 130.47, 128.98, 125.53, 52.48, 46.94, 41.27, 28.45, 24.93, 22.86, 22.31, 20.08, 20.06; IR (CHCl₃) 3400, 1653 cm$^{-1}$; LRMS (EI, 20 eV) m/z 503 (M+); HRMS (EI, 20 eV) for $C_{28}H_{46}N_4O_4$ (M+): calculated 502.3519. found 502.3486.

Preparation of Example 9

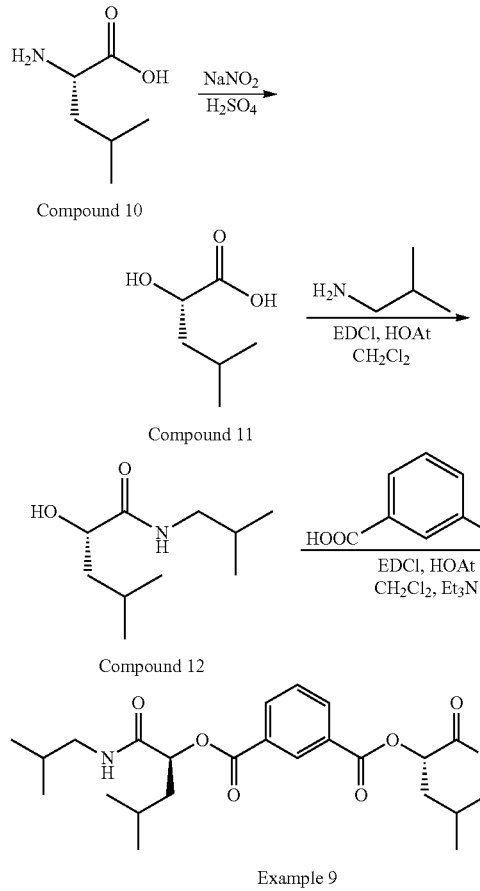

Compound 10

Compound 11

Compound 12

Example 9

Example 9 was prepared according to Scheme I above. Concentrated sulphuric acid (0.48 mL) was added cautiously to water (22 mL) in a 100 mL round-bottom flask containing L-leucine (Compound 10) (787 mg, 6.0 mmol). A solution of $NaNO_2$ (1.24 g, 18 mmol) in water (40 mL) was added through a dropping funnel at such a rate that the temperature of the reaction mixture does not exceed 5° C. After stirred at 0° C. for 1 hour, the reaction mixture was slowly warmed to room temperature and stirred for another 1 hour. The product was extracted with ethyl acetate and the organic layer was washed with brine and then dried over anhydrous $MgSO_4$. The organic solvent was evaporated off to give a sticky light yellow oil Compound 11, which was used directly in the next step.

Freshly distilled $CH_2Cl_2$ (50 mL) was added to a flask containing Compound 11 under nitrogen atmosphere, followed by the addition of HOAt (1.06 g, 7.8 mmol), isobutylamine (0.63 mL, 6.3 mmol), and finally EDCI (2.68 g, 9.0 mmol). After being stirred overnight, the reaction mixture was diluted with $CH_2Cl_2$. The organic layer was washed with 5% $NaHCO_3$ and brine, then dried over anhydrous $MgSO_4$ and concentrated to afford Compound 12 as a white solid, which was used directly in the next step without further purification.

Freshly distilled $CH_2Cl_2$ (50 mL) was added to a flask containing Compound 12 under nitrogen atmosphere, followed by the addition of HOAt (1.06 g, 7.8 mmol), isophthalic acid (500 mg, 3 mmol), triethylamine (0.82 mL, 6.0 mmol), and finally EDCI (2.68 g, 9.0 mmol). After stirred overnight, the reaction mixture was diluted with $CH_2Cl_2$. The organic layer was washed with 5% $NaHCO_3$ and brine, then dried over anhydrous $MgSO_4$ and concentrated. The crude oil was purified by flash column chromatography to afford Example 9 (1.02 g, 68%) as a white solid. Example 9 was characterized by the following data: m.p. 137-139° C.; $[\alpha]^{20}_D$+22.6° (c 1.00, $CHCl_3$); $^1H$ NMR (400 MHz, $CDCl_3$) δ 8.74 (t, J=1.6 Hz, 1H), 8.32 (dd, J=7.8, 1.7 Hz, 2H), 7.63 (t, J=7.8 Hz, 1H), 6.06 (t, J=5.7 Hz, 2H), 5.43 (dd, J=9.4, 3.9 Hz, 2H), 3.11 (t, J=6.6 Hz, 4H), 1.96-1.75 (m, 8H) 1.00-0.97 (m, 12H), 0.90-0.87 (m, 12H); $^{13}C$ NMR (100 MHz, $CDCl_3$) δ 169.78, 164.66, 134.48, 130.85, 130.08, 129.20, 74.03, 46.50, 40.78, 28.45, 24.73, 23.13, 21.81, 19.94; IR ($CHCl_3$) 3450, 1729, 1679 $cm^{-1}$; LRMS (EI, 20 eV) m/z 504 (M+); HRMS (EI, 20 eV) for $C_{28}H_{44}N_2O_6$ (M+): calculated 504.3199. found 504.3199.

Alternative Preparation Method for Example 2

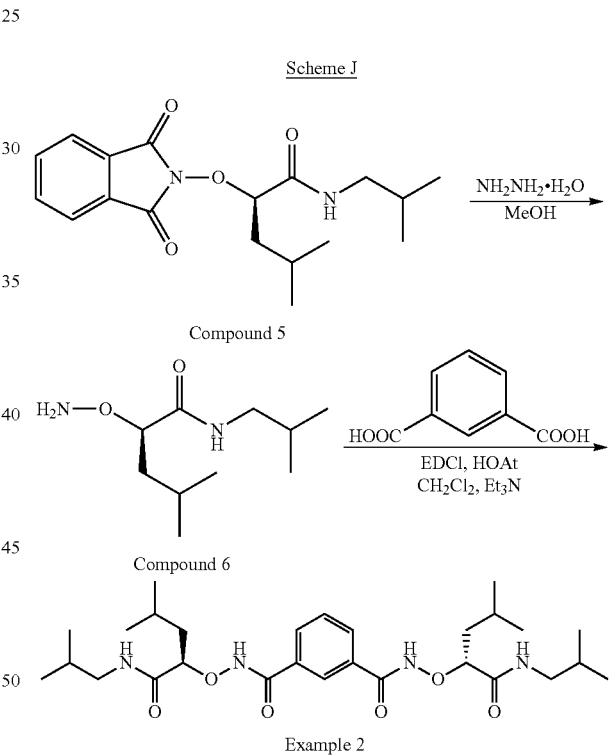

Compound 5

Compound 6

Example 2

Example 2 was also prepared according to Scheme J above which was similar to Scheme G for Example 7 except that pyridine-2,6-dicarboxylic acid was replaced with isophthalic acid. Example 2 was isolated as a white solid which was characterized by the following data: m.p. 176-178° C.; $[\alpha]^{20}_D$ (deg $cm^3$ $g^{-1}$ $dm^{-1}$)+67.3° (c=0.01 g $cm^{-3}$ in $CHCl_3$); $^1H$-NMR (600 MHz, $CDCl_3$) δ 10.43 ppm (s, 2H), 8.12 (s, 1H), 8.07 (t, J=5.7 Hz, 2H), 8.04 (d, J=7.8 Hz, 2H), 7.57 (t, J=7.8 Hz, 1H), 4.40 (dd, J=9.5, 3.4 Hz, 2H), 3.05-3.01 (m, 2H), 2.91-2.88 (m, 2H), 1.86-1.62 (m, 8H), 0.92 (d, J=6.6 Hz, 12H), 0.84 (d, J=6.7 Hz, 6H), 0.78 (d, J=6.7 Hz, 6H); $^{13}C$-NMR (75 MHz, $CDCl_3$) δ 171.89, 166.14, 131.97, 131.30, 129.69, 124.93, 85.60, 46.69, 41.15, 28.29, 24.85, 23.18, 21.81, 20.04, 19.99; IR (CHCl$_3$) 3.332 cm$^{-1}$, 3.185, 1.663 (C=O) cm$^{-1}$; LRMS (EI, 20 eV) m/z 534 (M$^+$); HRMS (EI, 20 eV) (m/z): [M$^+$] calculated for C$_{28}$H$_{46}$N$_4$O$_6$, 534.3417. found 534.3435.

Preparation of Example 10

Scheme K

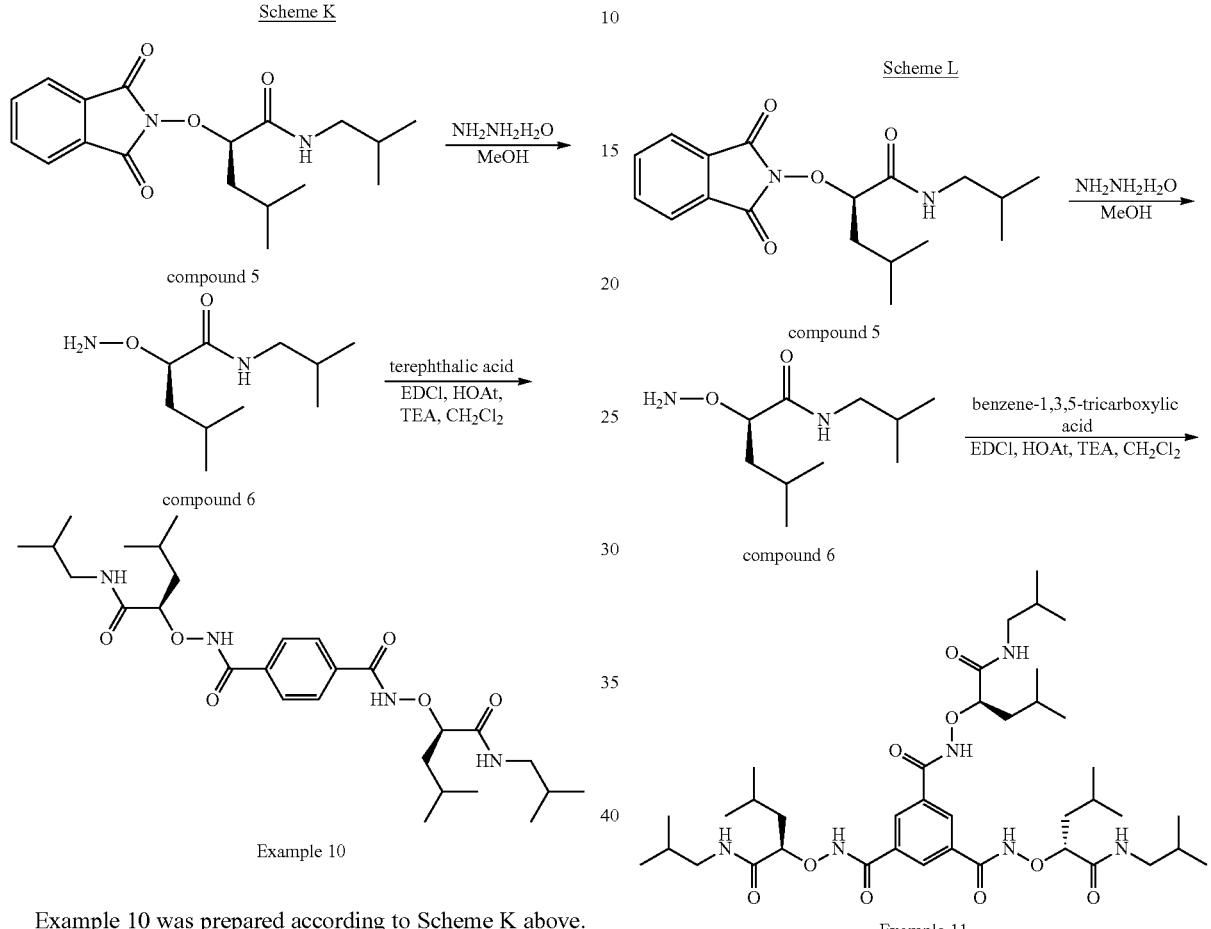

Example 10

Example 10 was prepared according to Scheme K above. To a solution of Compound 5 (332 mg, 1 mmol) in CH$_3$OH (10 mL) was added NH$_2$NH$_2$—H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (1-hydroxy-7-azabenzotriazole, CAS No. 39968-33-7, 177 mg, 1.3 mmol), terephthalic acid (83 mg, 0.5 mmol), triethylamine (0.14 mL, 1.0 mmol), and finally EDCI (447 mg, 1.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford Example 10 (107 mg, 40%) as a white solid. Example 10 was characterized by the following data: $^1$H NMR (300 MHz, DMSO-d$_6$) δ 12.03 (s, 2H), 8.24 (s, 2H), 7.82 (s, 4H), 4.38 (dd, J=8.5, 4.5 Hz, 2H), 2.96-2.90 (m, 4H), 1.83-1.50 (m, 8H), 0.98 (d, J=6.5 Hz, 6H) 0.93 (d, J=6.5 Hz, 6H), 0.81 (d, J=6.6 Hz, 6H), 0.79 (d, J=6.6 Hz, 6H); $^{13}$C NMR (75 MHz, DMSO-d$^6$) δ 170.93, 164.99, 135.00, 127.79, 84.01, 46.25, 28.42, 24.66, 23.47, 22.47, 20.40, 20.16; LRMS (ESI) m/z 557 (M$^+$+Na);

Preparation of Example 11

Scheme L

Example 11

Example 11 was prepared according to Scheme L above. To a solution of Compound 5 (332 mg, 1 mmol) in CH$_3$OH (10 mL) was added NH$_2$NH$_2$—H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (1-hydroxy-7-azabenzotriazole, 177 mg, 1.3 mmol), benzene-1,3,5-tricarboxylic acid (105 mg, 0.5 mmol), triethylamine (0.14 mL, 1.0 mmol), and finally EDCI (dichloroethane, 447 mg, 1.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford Example 11 (171 mg, 45%) as a white solid. Example 11 was characterized by the following data: $^1$H NMR (400 MHz, DMSO-d$_6$) δ 12.14 (s, 3H), 8.26 (s, 3H), 8.22 (s, 3H), 4.38 (dd, J=8.4, 4.0 Hz, 3H), 3.00-2.89 (m, 6H), 1.85-1.51 (m, 12H), 0.98 (d, J=6.5 Hz, 9H), 0.93 (d, J=6.6 Hz, 9H), 0.81 (d, J=7.0 Hz, 9H), 0.79 (d, J=8.0 Hz, 9H); $^{13}$C NMR (100 MHz, DMSO-d$_6$) δ 170.97, 164.43, 132.80, 129.45, 84.19, 46.25, 28.43, 24.69, 23.48, 22.42, 20.40; LRMS (ESI) m/z 762 (M$^+$);

Preparation of Examples 12 and 13

10.60 (br, 1H), 10.49 (br, 1H), 8.07 (br, 1H), 7.88 (br, 1H), 6.88 (dt, J=15.4, 6.9 Hz, 1H), 5.89 (d, J=15 Hz, 1H), 4.28 (d, J=5.2 Hz, 2H), 3.11-2.97 (m, 6H), 1.84-1.60 (m, 8H), 0.95-0.87 (m, 24H); $^{13}$C NMR (100 MHz, CDCl$_3$) δ 171.97, 167.92, 137.25, 123.45, 85.31, 85.22, 46.70, 46.66, 40.98, 28.34, 24.71, 23.16, 21.71, 20.07; LRMS (ESI) m/z 521 (M$^+$+Na).

Example 12 (40 mg, 0.08 mmol) was dissolved in 1 mL MeOH, 4 mg 10% Pd/C was added to the mixture, then the mixture stirred with H$_2$ at room temperature under balloon pressure overnight. The reaction mixture was filtered through celite and concentrated to afford Example 13 (40 mg, quant).

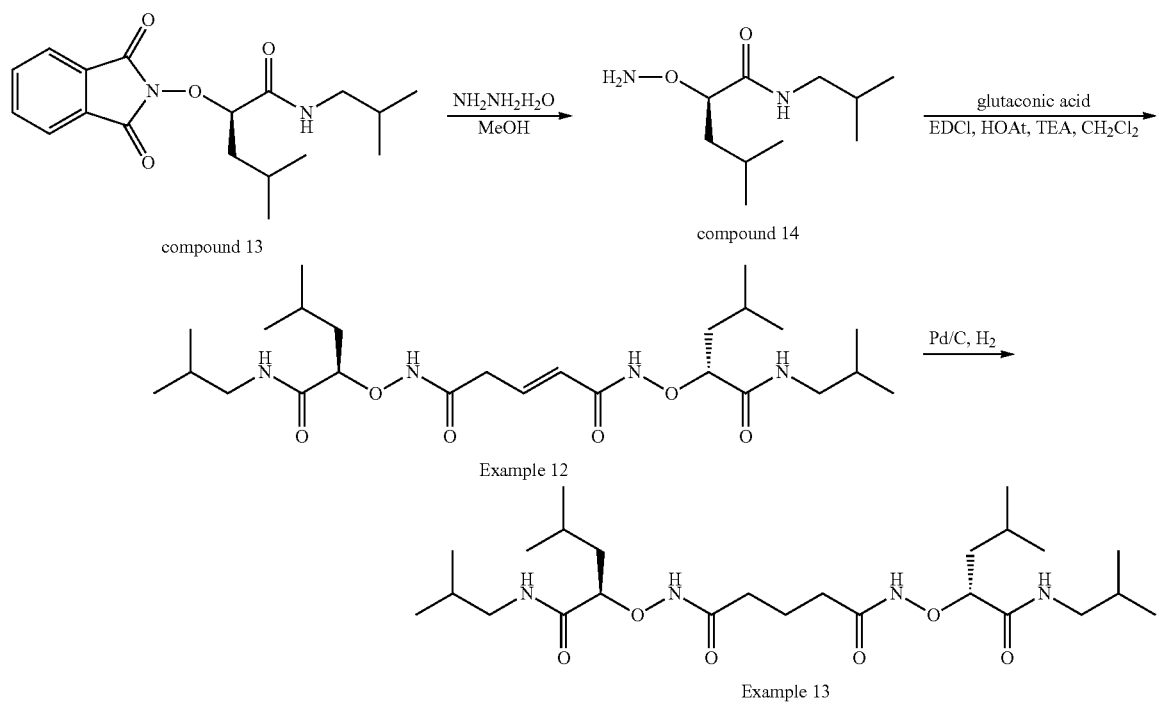

Scheme M

Examples 12 and 13 were prepared according to Scheme M above. To a solution of Compound 5 (332 mg, 1 mmol) in CH$_3$OH (10 mL) was added NH$_2$NH$_2$·H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (1-hydroxy-7-azabenzotriazole, 177 mg, 1.3 mmol), glutaconic acid (65 mg, 0.5 mmol), triethylamine (0.14 mL 1.0 mmol), and finally EDCI (dichloroethane, 447 mg, 1.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford Example 12 (40 mg, 16%) as a white solid. Example 12 was characterized by the following data: $^1$H NMR (300 MHz, CDCl$_3$) δ

Example 13 was characterized by the following data: $^1$H NMR (300 MHz, CDCl$_3$) δ 7.69 (br, 2H), 4.35 (dd, J=8.6, 3.8 Hz, 2H), 3.29-3.24 (m, 2H), 2.87-2.85 (m, 2H), 2.18-2.16 (m, 2H), 1.88-1.63 (m, 12H), 1.00-0.92 (m, 24H); $^{13}$C NMR (75 MHz, CDCl$_3$) δ 172.72, 170.30, 86.21, 46.59, 40.77, 30.58, 28.44, 24.75, 23.04, 21.80, 20.71, 20.05; LRMS (ESI) m/z 523 (M$^+$+Na).

Example 14 pH-Stat Fluorometric Transport Assay

This Example illustrates that the compound of Example 2 mediates chloride release when incorporated into liposomes. The liposome-based pH-stat fluorometric assay is an assay routinely used for identification of physiologically relevant ionophores, which are disclosed in (a) Deng, G., Dewa, T. and Regen, S. L. *J. Am. Chem. Soc.* 1996, 118, 8975; (b) Schlesinger, P. H., Ferdani, R., Liu, J., Pajewska, J., Pajewski, R., Saito, M., Shabany, H. and Gokel, G. W. *J. Am. Chem. Soc.* 2002, 124, 1848; (c) Sidorov, V., Kotch, F. W., Abdrakhmanova, G., Mizani, R., Fettinger, J. C. and Davis, J. T. *J. Am. Chem. Soc.* 2002, 124, 2267; (d) Sidorov, V., Kotch, F. W., Kuebler, J. L., Lam, Y.-F. and Davis, J. T. *J. Am. Chem. Soc.* 2003, 125, 2840; and (e) Baumeister, B., Sakai, N. and Matile, S. *Angew. Chem., Int. Ed.* 2000, 39, 1955, all of which are incorporated herein by reference. For example, in this assay, a controlled amount of the base and potential ionophore is added to a suspension of liposomes containing a pH-sensitive dye, 8-hydroxypyrene-1,3,6-trisulfonate (HPTS, pyranine). The resulting pH gradient across the bilayer membrane causes the efflux of hydronium ions or the influx of hydroxide ions and builds up an electrostatic potential. This potential can be compensated by the efflux of anions or influx of cations ($H^+/M^+$ or $OH^-/A^-$ antiport and $H^+/A^-$ or $M^+/OH^-$ symport mechanisms are possible). If the compound of interest mediates such ion transport, the efflux of hydronium ions or the influx of hydroxide ions continues altering the intravascular pH and the fluorescence of the reporter dye.

Figure 5:
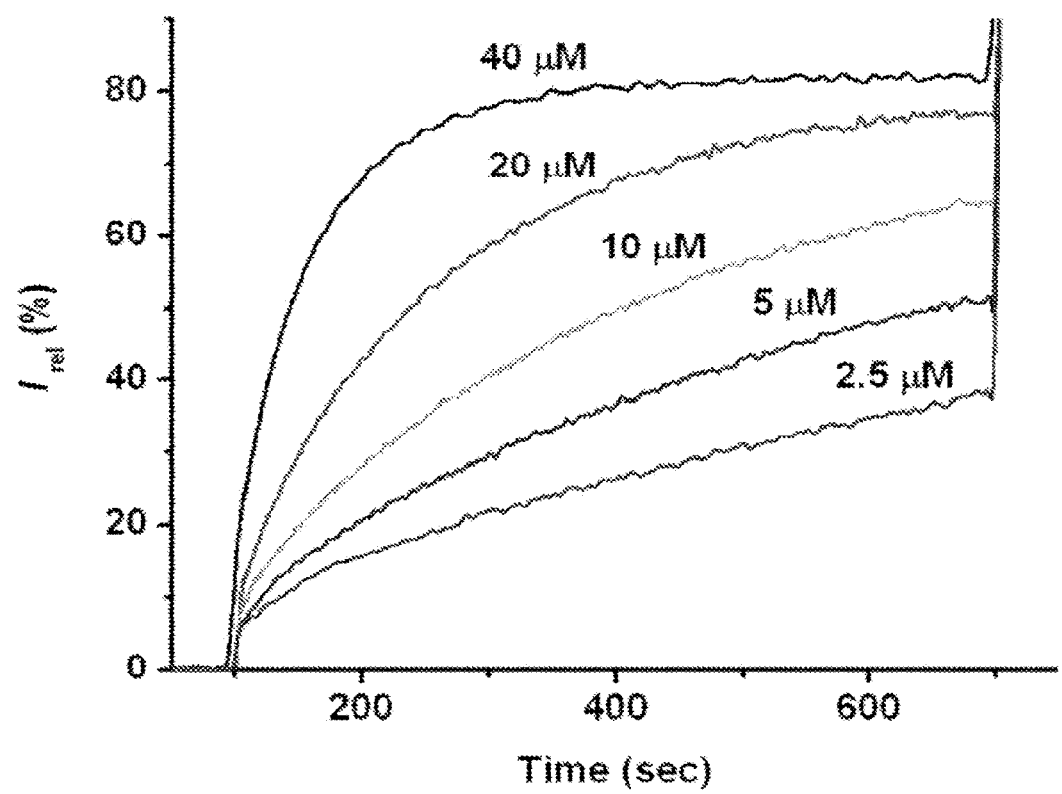
FIG. 5 shows chloride release mediated by Example 2 at different concentrations from large unilamellar vesicles (LUVs), where NaCl extra- and intravesicular buffers were used. The experimental details are described in Example 14.
Figure 6:
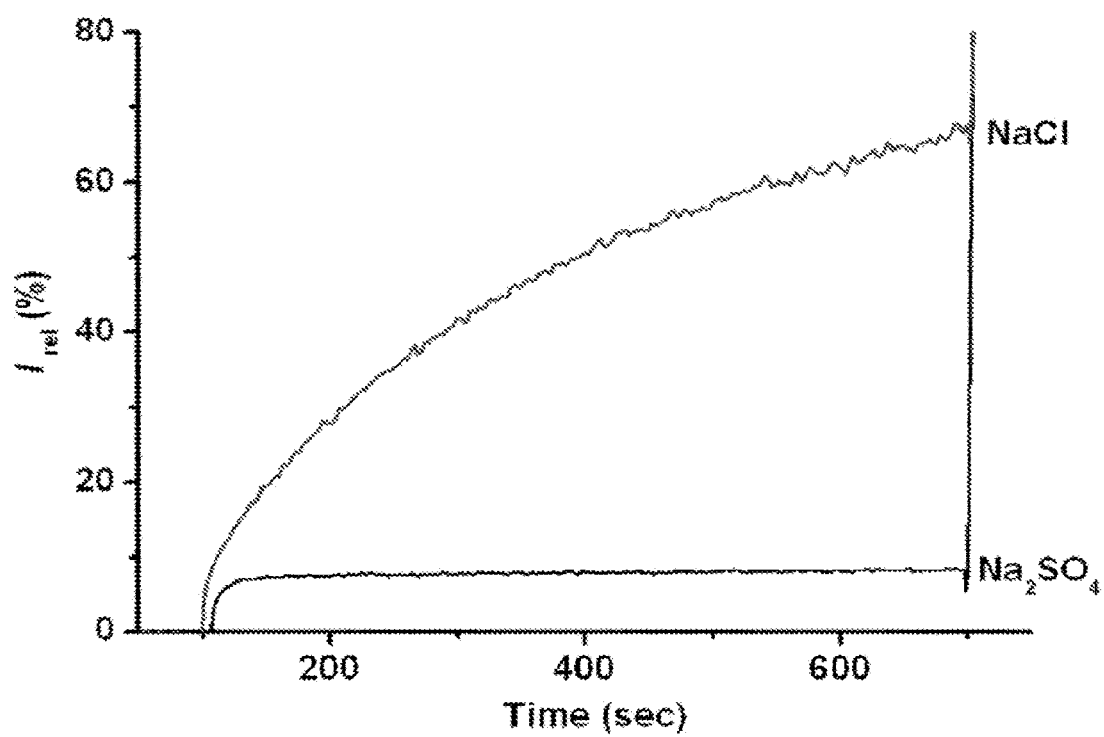
FIG. 6 shows Example 2 mediated electrolyte exchange in the presence of chloride but not in the presence of sulfate. The experimental details are described in Example 14.
Figure 7:
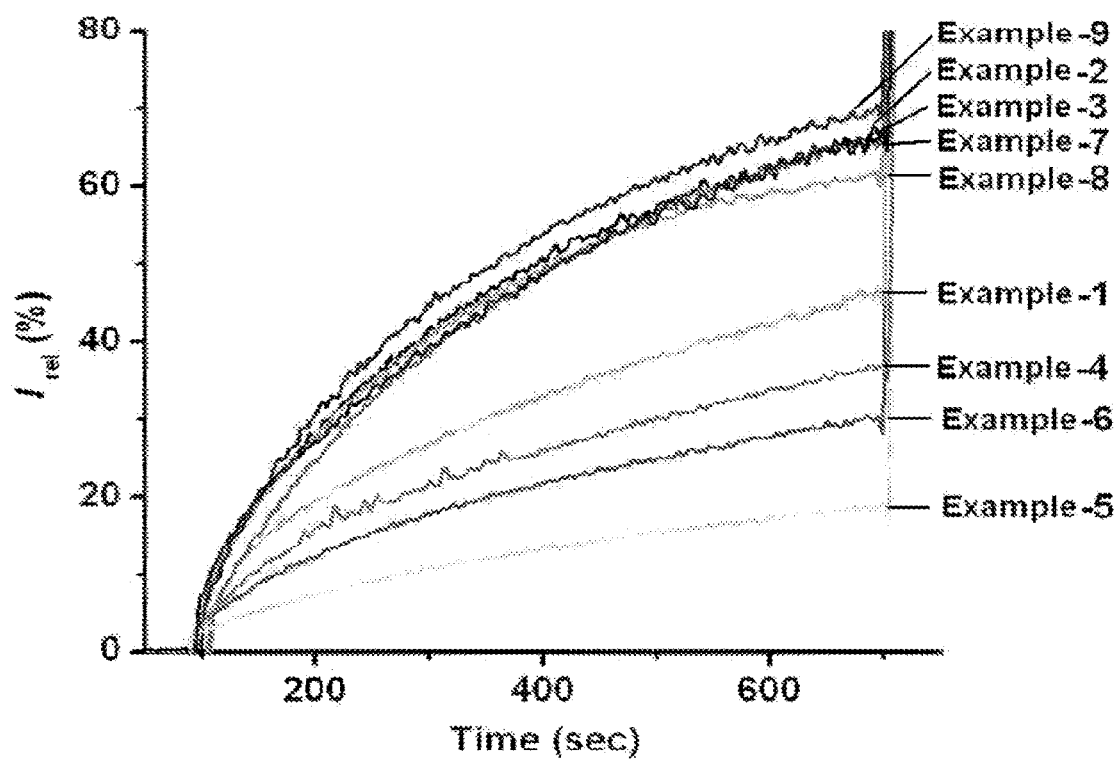
FIG. 7 shows chloride transport ability of different synthetic ion channels derived from Examples 1-9 in LUVs, where NaCl extra- and intravesicular buffers were used.
Figure 12:
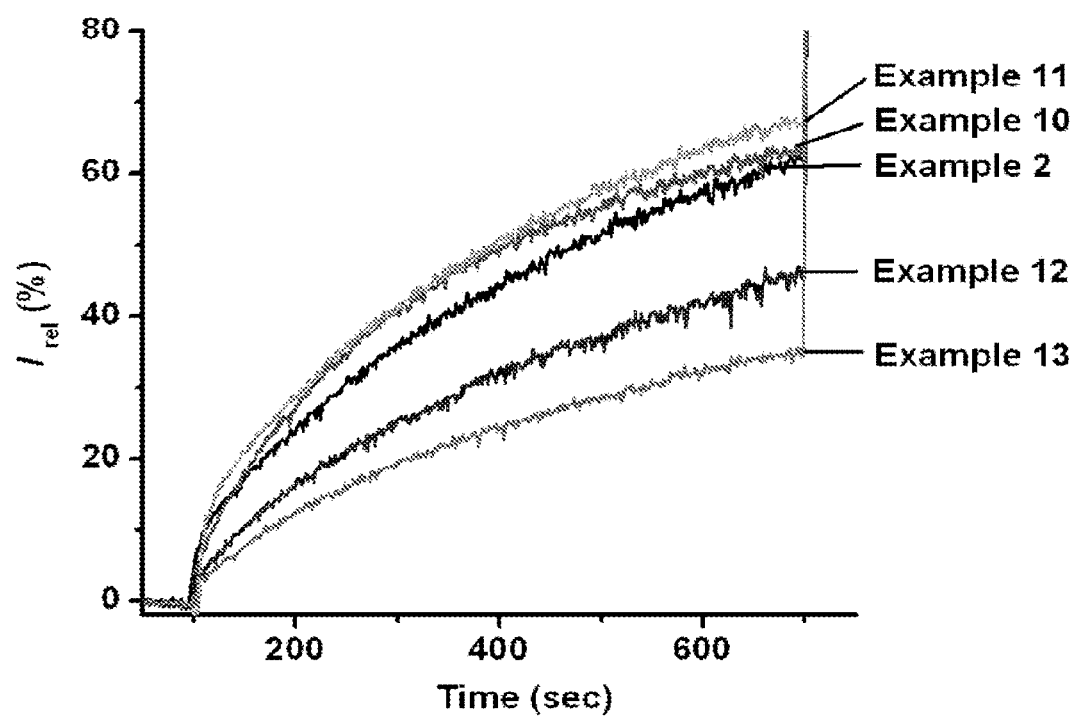
FIG. 12 shows chloride transport ability of different synthetic ion channels derived from Examples 2 and 10-13 in LUVs, where NaCl extra- and intravesicular buffers were used.

Example 2-mediated chloride release was determined in large unilamellar vesicles (LUVs) of 100 nm average dimension, as reported in Sidorov, V., Kotch, F. W., Abdrakhmanova, G., Mizani, R., Fettinger, J. C. and Davis, J. T. *J. Am. Chem. Soc.* 2002, 124, 2267. FIG. 5 shows that the application of Example 2 resulted in rapid, concentration-dependent exchange between extra- and intravesicular electrolytes. Importantly, Example 2 mediated electrolyte exchange with high anion selectivity. It mediated electrolyte exchange in the presence of chloride but not in the presence of sulfate (see FIG. 6). In contrast to the results shown in FIG. 6, where NaCl extra- and intravesicular buffers were used, no transport activity was detected in LUVs symmetrically loaded with $Na_2SO_4$. This anion-dependent activity is a strong evidence that Example 2 mediates chloride transport across the bilayer. FIG. 7 shows that in addition to Example 2, Examples 1 and 3-9 can also mediate chloride transport across lipid bilayers of chloride-containing liposomes with different efficiencies. FIG. 12 shows that in addition to Example 2, Examples 10-13 can also mediate chloride transport across lipid bilayers of chloride-containing liposomes with different efficiencies.

Example 15

Example 15 shows that the compound of Example 2 can function as a voltage-dependent chloride-selective channel when partitioned into lipid bilayers. Single-channel recording, using patch clamp techniques, is the most critical test for identifying ion channel formation, which is distinguished from other ion transport mechanisms such as ion carriers, and quantifying ion transport efficiency of a membrane channel. The channel-forming activity of Example 2 incorporated in lipid bilayers is examined using patch-clamp technique on giant liposomes. Characteristic single-channel currents were recorded with primary conductance of 54 pS in symmetric 0.2 M N-methyl-glucamine hydrochloride (NMDG-Cl) solutions when application of Example 2 in bath solution (FIG. 8), indicating that Example 2 can partition into lipid bilayers of liposomes efficiently and thereby forms ionic channels.

Figure 8:
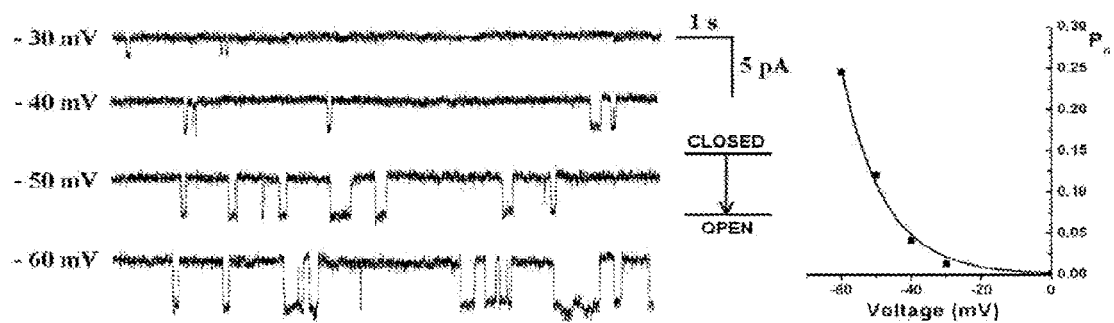
FIG. 8 shows single-channel recording results illustrating that Example 2 can mediate chloride transport across lipid bilayer by an ion channel mechanism featuring voltage-dependent gating property. The experimental details are described in Example 15.

The two key properties of ion channels in nature are ion selectivity, that is, a channel permits only certain ionic species to flow through its pore, and gating referring to the mechanism of channel opening and closing. The ion channels formed by Example 2 turned out to be anion selective and voltage-gated. There was no measurable change either in conductance or in reversal potential when NMDG-Cl in the bath solution was replaced by potassium chloride (KCl), suggesting that these channels are not permeable to K ions. The channel open probability ($P_o$) and frequency were enhanced steeply upon increasing voltages of lipid bilayers within a physiologically relevant range of voltages, suggesting voltage-dependent gating (FIG. 8).

Example 16

Example 16 shows that the compound of Example 2 partitions into human cell membranes and dramatically increases cell chloride currents. The whole-cell configuration of the patch-clamp technique was used to examine the electrophysiological properties of the ionic currents induced by Example 2 in human embryonic kidney (HEK 293) cells. HEK 293 cell line originally obtained from the American Type Culture Collection, were cultured in DMEM supplemented with 10% FBS and 100 IU/ml penicillin G and 0.1 mg/ml streptomycin. Cells were grown at 37° C. in a 5% $CO_2$ humidified incubator. Whole-cell chloride currents were recorded by using an EPC 9 patch clamp amplifier (HEKA Elektronik, Lambrecht/Pfalz, Germany) in voltage-clamp mode, controlled by Pulse/PulseFit 8.7 software (HEKA). Patch pipettes (resistance, 3-5 MΩ) were filled with a solution internal pipette solution containing CsCl 140, $MgCl_2$ 1, HEPES 10, EGTA 5, $Na_2ATP$ 5 (in mmol/L, pH 7.2 with CsOH). The bath solution contained NaCl 140, CsCl 5, $CaCl_2$ 1, $MgCl_2$ 1, HEPES 10 (in mmol/L, pH 7.4 with CsOH). After gigaohm seals were obtained, the membrane was ruptured with a pulsed negative pressure. Pipette and membrane capacitance were automatically compensated. Series resistance was typically compensated by 70%. The cells were held at 0 mV and voltage steps ranging from −80 to +80 mV were applied for 800 ms in 20 mV step increments. All macroscopic currents were sampled at 50 kHz and filtered at 5 kHz, and data were analyzed with PulseFit (HEKA). Changes of Cl current were detected from the same cells before and after exposure to the bath solution containing Example 2 at the concentration of 50 nM. All experiments were performed at room temperature (22-25° C.)

Figure 9:
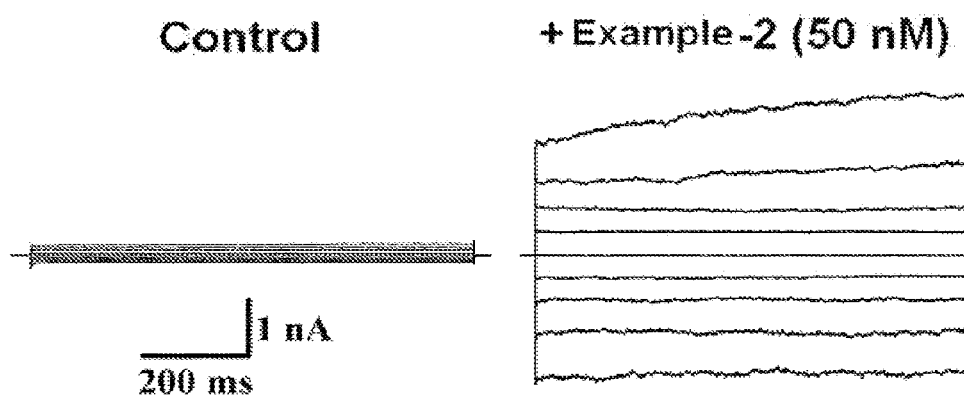
FIG. 9 shows whole-cell recording results illustrating that Example 2 can increase cell chloride currents when partitioned into human cell membranes. The experimental details are described in Example 16.

At a low concentration of 50 nM, Example 2 caused a large increase in whole cell currents (FIG. 9), indicating that Example 2 may mediate Cl ions transport efficiently across cell membranes of HEK 293 cells. In addition, the induced currents were not reduced in the presence of a cellular anion transport inhibitor such as 4,4'-diisothiocyanatostilbene-2,2'-disulfonate (DIDS). This property rules out that Example 2 may increase whole cell currents by activating the natural chloride channels in HEK 293 cells and suggests that the synthetic chloride channels formed by Example 2 indeed accounts for the observed currents.

Example 17

Example 17 shows the chloride transport activity of the compound of Example 2 in liposome with chloride-sensitive fluorescent indicator SPQ.

Liposome Preparation:

Egg yolk L-α-phosphatidylcholine (EYPC, 91 mg, 120 μmol) was dissolved in a $CHCl_3$/MeOH mixture, the solution was evaporated under reduced pressure and the resulting thin film was dried under high vacuum for 3 hours. The lipid film was hydrated in 1.2 mL of solution A (200 mM $NaNO_3$, 0.5 mM SPQ) for 2 hours. During hydration, the suspension was submitted to 5 freeze-thaw cycles (liquid nitrogen, water at room temperature). The large multilamellar liposome suspension (1 mL) was submitted to high-pressure extrusion at room temperature (>21 extrusions through a 0.1 μm polycarbonate membrane afforded a suspension of large unilamellar vesicles (LUVs) with an average diameter of 100 nm). The LUV suspension was separated from extravesicular dye by size exclusion chromatography (SEC) (stationary phase: Sephadex G-50, mobile phase: solution B: 20 mM NaNO3) and diluted with the solution B to give a stock solution with a lipid concentration of 10 mM (assuming 100% of lipid was incorporated into liposomes).

Figure 10:
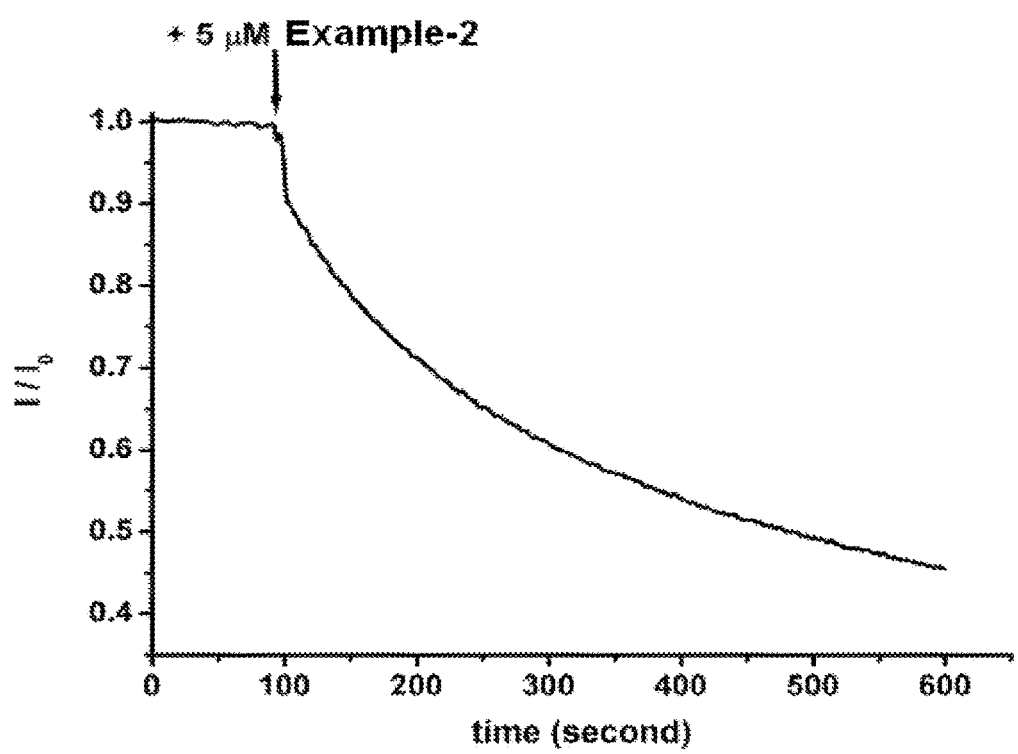
FIG. 10 shows the chloride transport activity of Example 2 in liposome with chloride-sensitive fluorescent indicator SPQ.

Fluorescent Assay:

Typically, 100 μL of SPQ-loaded vesicles (stock solution) was suspended in 1.9 mL of solution C (200 mM NaCl) and placed into a fluorimetric cell. SPQ emission at 430 nm was monitored with excitation wavelengths at 360 nm. At 100 seconds, 20 μL of a 0.5 mM THF solution of Example 2 was added through an injection port. The results are shown in FIG. 10.

Example 18

Figure 11:
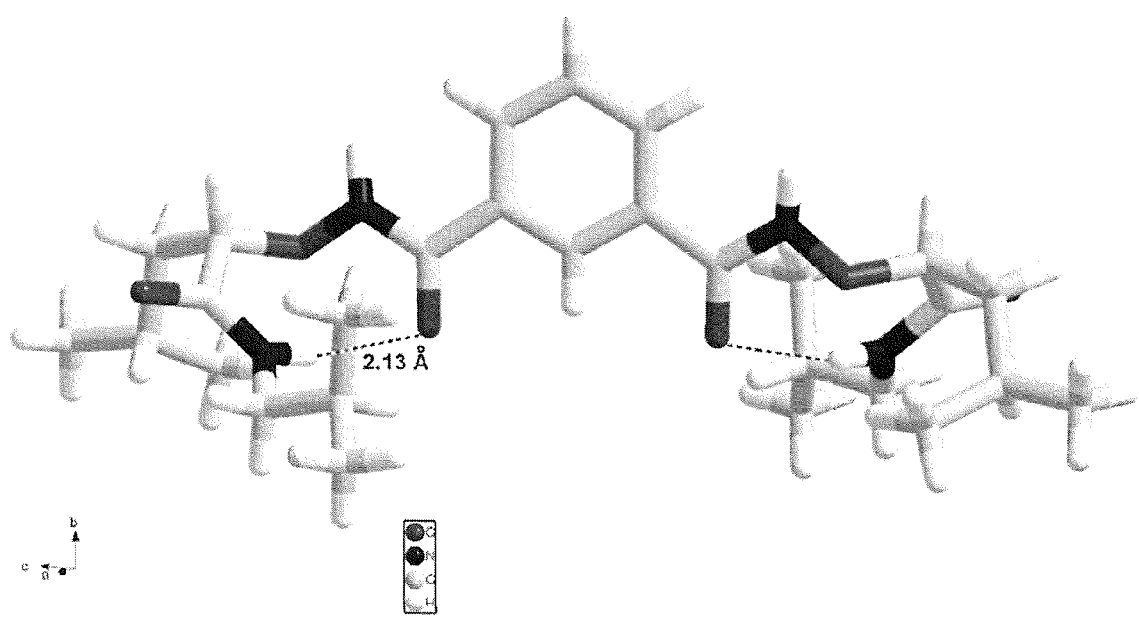
FIG. 11 shows the X-ray crystal structure of Example 2

Example 18 shows the X-ray crystallographic analysis of example 2. The X-ray crystal structure of Example 2 is shown in FIG. 11. The other X-ray crystallographic data and data collection method are shown below.

Data Collection:

A crystal of dimensions 0.4×0.35×0.1 mm mounted on a glass fibre was used for data collection at −20° C. on a MAR diffractometer with a 300 mm image plate detector using graphite monochromatized Mo—$K_+$ radiation (=0.71073 Å). Data collection was made with 2° oscillation step of φ, 15 minutes exposure time and scanner distance at 120 mm. One hundred images were collected.

Crystal Data:

[$C_{28}H_{46}N_4O_6$]; formula weight=534.69, Orthorhombic, C 2 2 $2_1$, a=7.725 (2) Å, b=18.967 (4) Å, c 21.145 (4) Å, V=3098.2 (11) Å$^3$, Z=$D_c$=1.146 g cm$^{-3}$, μ(Mo—Kα)=0.081 mm$^{-1}$, F(000)=1160, T=253 K.

TABLE 1

Crystal data and structure refinement for Example 2.

| | |
|---|---|
| Empirical formula | $C_{28}H_{46}N_4O_6$ |
| Formula weight | 534.69 |
| Temperature | 253(2) K |
| Wavelength | 0.71073 Å |
| Crystal system | Orthorhombic |
| Space group | C 2 2 $2_1$ |
| Unit cell dimensions | a = 7.725(2) Å   α = 90°. |
| | b = 18.967(4) Å  β = 90°. |
| | c = 21.145(4) Å  γ = 90°. |
| Volume | 3098.2(11) Å$^3$ |
| Z | 4 |
| Density (calculated) | 1.146 Mg/m$^3$ |
| Absorption coefficient | 0.081 mm$^{-1}$ |
| F(000) | 1160 |

TABLE 1-continued

Crystal data and structure refinement for Example 2.

| | |
|---|---|
| Crystal size | 0.4 × 0.35 × 0.1 mm$^3$ |
| Theta range for data collection | 1.93 to 25.35°. |
| Index ranges | −7 <= h <= 7, −21 <= k <= 21, −24 <= l <= 24 |
| Reflections collected | 7174 |
| Independent reflections | 2039 [R(int) = 0.0498] |
| Completeness to theta = 25.35° | 75.2% |
| Absorption correction | None |
| Refinement method | Full-matrix least-squares on F$^2$ |
| Data/restraints/parameters | 2039/2/185 |
| Goodness-of-fit on F$^2$ | 0.969 |
| Final R indices [I > 2sigma(I)] | R1 = 0.0497, wR2 = 0.1217 |
| R indices (all data) | R1 = 0.0707, wR2 = 0.1310 |
| Absolute structure parameter | 1(2) |
| Largest diff. peak and hole | 0.365 and −0.284 e · Å$^{-3}$ |

In other embodiments, $H_{DA}$ of formula (I) is a divalent group having formula (X):

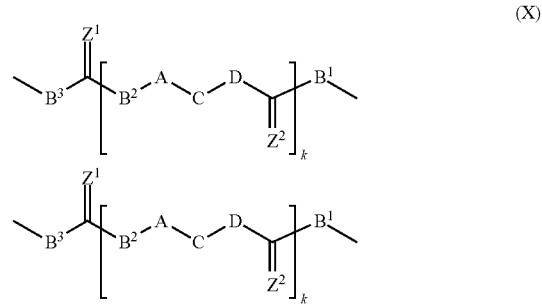

wherein
wherein each of $Z^1$ and $Z^2$ is independently O, S or $NR^1$;
each of A, $B^1$, $B^2$, $B^3$, C, and D is independently a bond, O, S, $NR^2$ or a substituted or unsubstituted $C_{1-10}$ alkylene; and
k is an integer from 1 to 20, where each of $R^1$ and $R^2$ is independently H, acyl, hydrocarbyl, carbocyclyl or heterocyclyl and at least one of $B^1$ and $B^2$ is NH.

In certain embodiments, at least one of each of A, $B^1$, $B^2$, $B^3$, C, and D is independently unsubstituted $C_{1-3}$ alkylene or $C_{1-3}$ alkylene substituted with at least an alkyl, aryl, substituted alkyl or substituted aryl group. In further embodiments, at least one of each of A, $B^1$, $B^2$, $B^3$, C, and D is independently $C_{1-3}$ alkylene substituted with at least an isobutyl group.

In certain embodiments, the self-assembling compound has one of the following formulae:

4.16

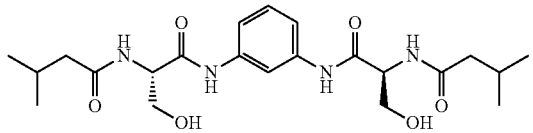

4.14

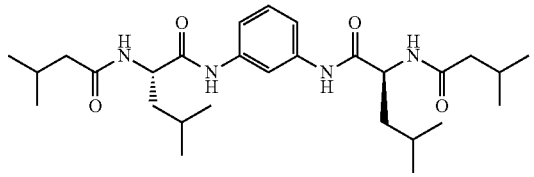

4.17

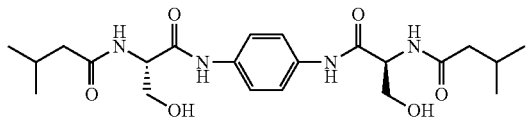

4.15

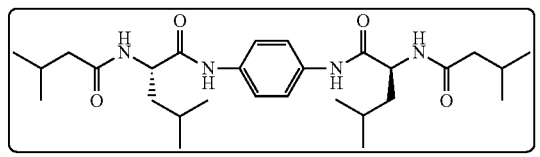

-continued
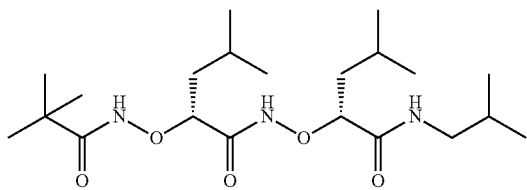
Dipep-1B
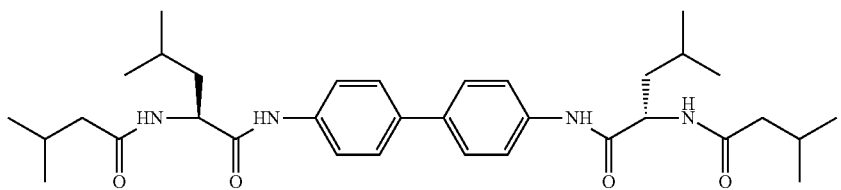
Dipep-1F
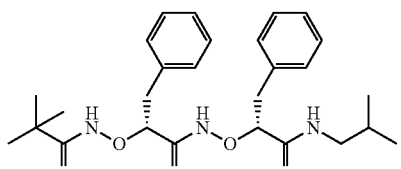
LPY-CM9
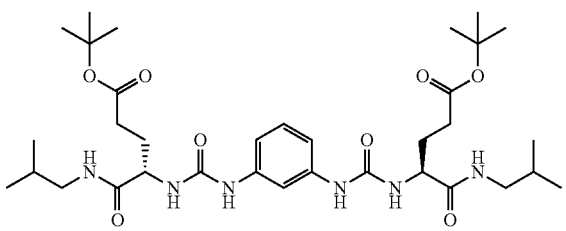
LPY-CM64
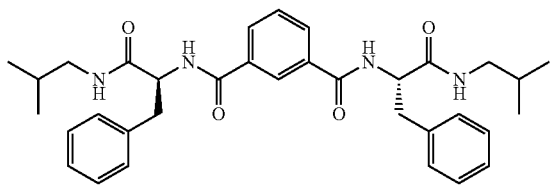
LPY-CM57
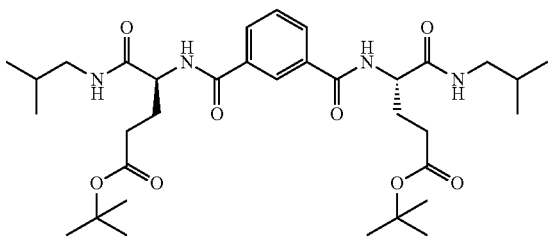
LPY-CM11
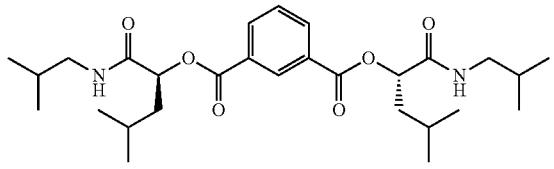
ZHY-CM11
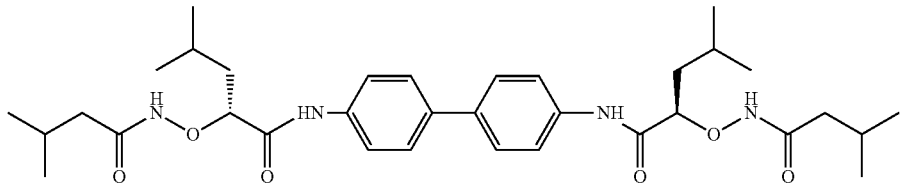
ZHY-CM23Cbz
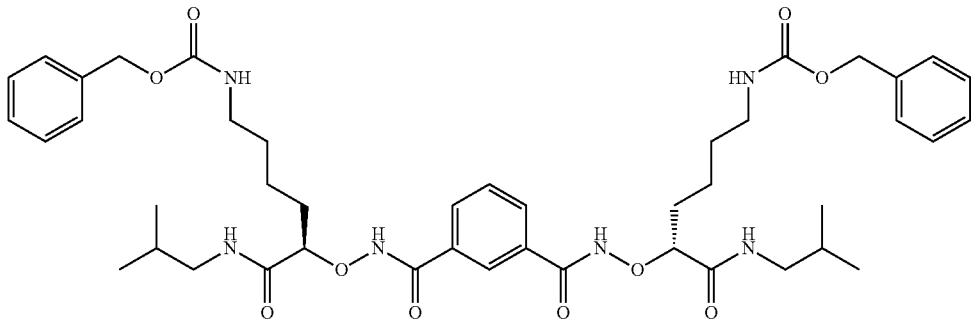

-continued
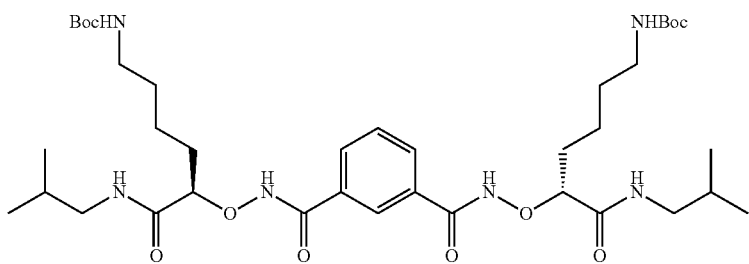
ZHY-CM23
4.11
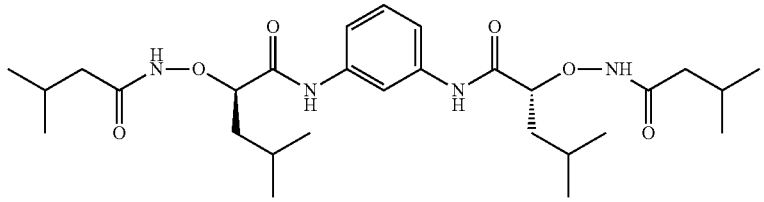
4.12
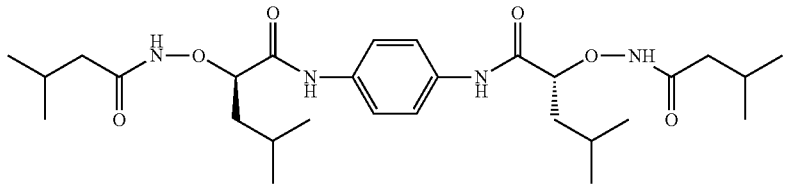
ZHY-CM12
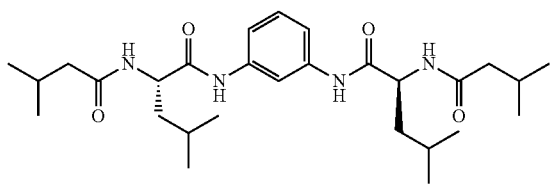
ZHY-CM13
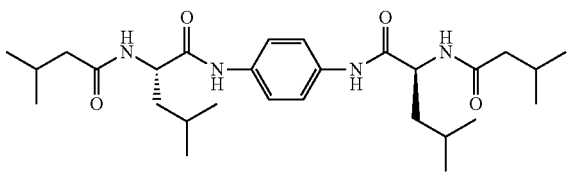
4.23 4.19
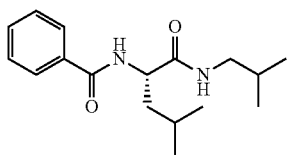
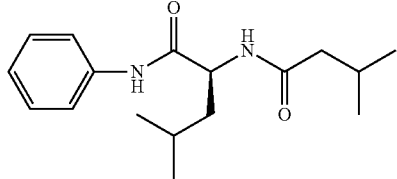
4.24
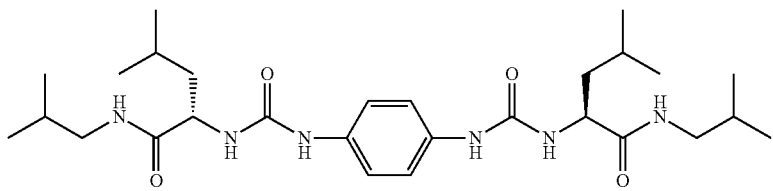
4.25 4.21
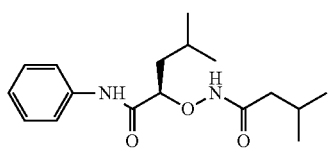
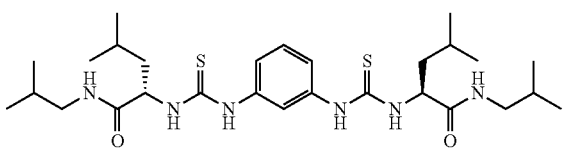

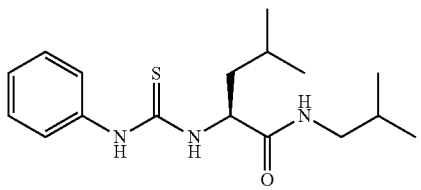

4.26

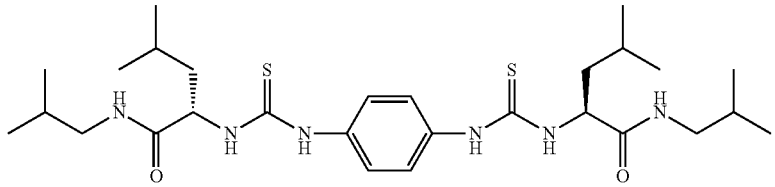

4.22

As demonstrated above, embodiments herein provide various self-assembling compounds which are useful for making ion-channel compositions and membranes comprising same. While this disclosure has been described with respect to a limited number of embodiments, the specific features of one embodiment should not 5 be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the 10 described embodiments exist. For example, the ion-channel compositions disclosed herein need not comprising only self-assembling compounds. It can comprise any type of compounds generally suitable for ion-channel compositions. It is noted that the methods for making and using the ion-channel compositions disclosed herein are described with reference to a number of steps. These steps can be practiced in any 15 sequence. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication 20 or patent application was specifically and individually indicated to be incorporated by reference. It is to be understood that this disclosure has been described in detailed by way of illustration and example in order to acquaint others skilled in the art with the invention, its principles, and its practical application. Further, the specific embodiments provided herein as set forth are not intended to be exhaustive or to limit the disclosure, 25 and that many alternatives, modifications, and variations will be apparent to those skilled in the art in light of the foregoing examples and detailed description. Accordingly, this disclosure is intended to embrace all such alternatives, modifications, and variations that fall within the spirit and scope of the following claims. While some of the examples and descriptions above include some conclusions about the way the compounds, compositions and methods may function, the inventors do not intend to be bound by those conclusions and functions, but put them forth only as possible explanations in light of current understanding.

We claim:

1. A self-assembling compound for the formation of ion channels in lipid bilayers or cell membranes having formula (I):

(I)

or a salt, solvate, polymorph or stereoisomer thereof,
wherein X is an unsubstituted or substituted hydrocarbyl or heterocyclyl;
n is an integer from 1 to 6;
Y is a monovalent, divalent, trivalent, tetravalent, pentavalent or hexavalent linking group formed by removing one, two, three, four, five and six hydrogen atoms respectively from an unsubstituted or substituted hydrocarbon or carbocycle; and
$H_{DA}$ is a divalent group having formula (II):

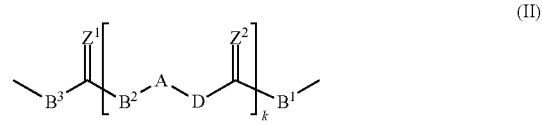

(II)

wherein each of $Z^1$ and $Z^2$ is independently O, S or $NR^1$;
each of A, $B^1$, $B^2$, $B^3$ and D is independently a bond, O, S, $NR^2$ or a substituted or unsubstituted $C_{1-10}$ alkylene; and
k is an integer from 1 to 20, where each of $R^1$ and $R^2$ is independently H, acyl, hydrocarbyl, carbocyclyl or heterocyclyl and at least one of $B^1$ and $B^2$ is NH.

2. The self-assembling compound of claim 1, wherein Y is a monovalent, divalent, trivalent, tetravalent, pentavalent or hexavalent linking group formed by removing one, two, three, four, five and six hydrogen atoms respectively from an unsubstituted or substituted hydrocarbon or carbocycle.

3. The self-assembling compound of claim 1, wherein at least one of $Z^1$ or $Z^2$ is S or $NR^1$.

4. The self-assembling compound of claim 1, wherein at least one of A, $B^2$, and D is O or S.

5. The self-assembling compound of claim 1, wherein each of A and D is a bond.

6. The self-assembling compound of claim 1, wherein each of $B^1$, $B^2$, and $B^3$ is independently NH.

7. The self-assembling compound of claim 1, wherein X is hydrocarbyl or substituted hydrocarbyl.

8. The self-assembling compound of claim 1, wherein the compound is selected from
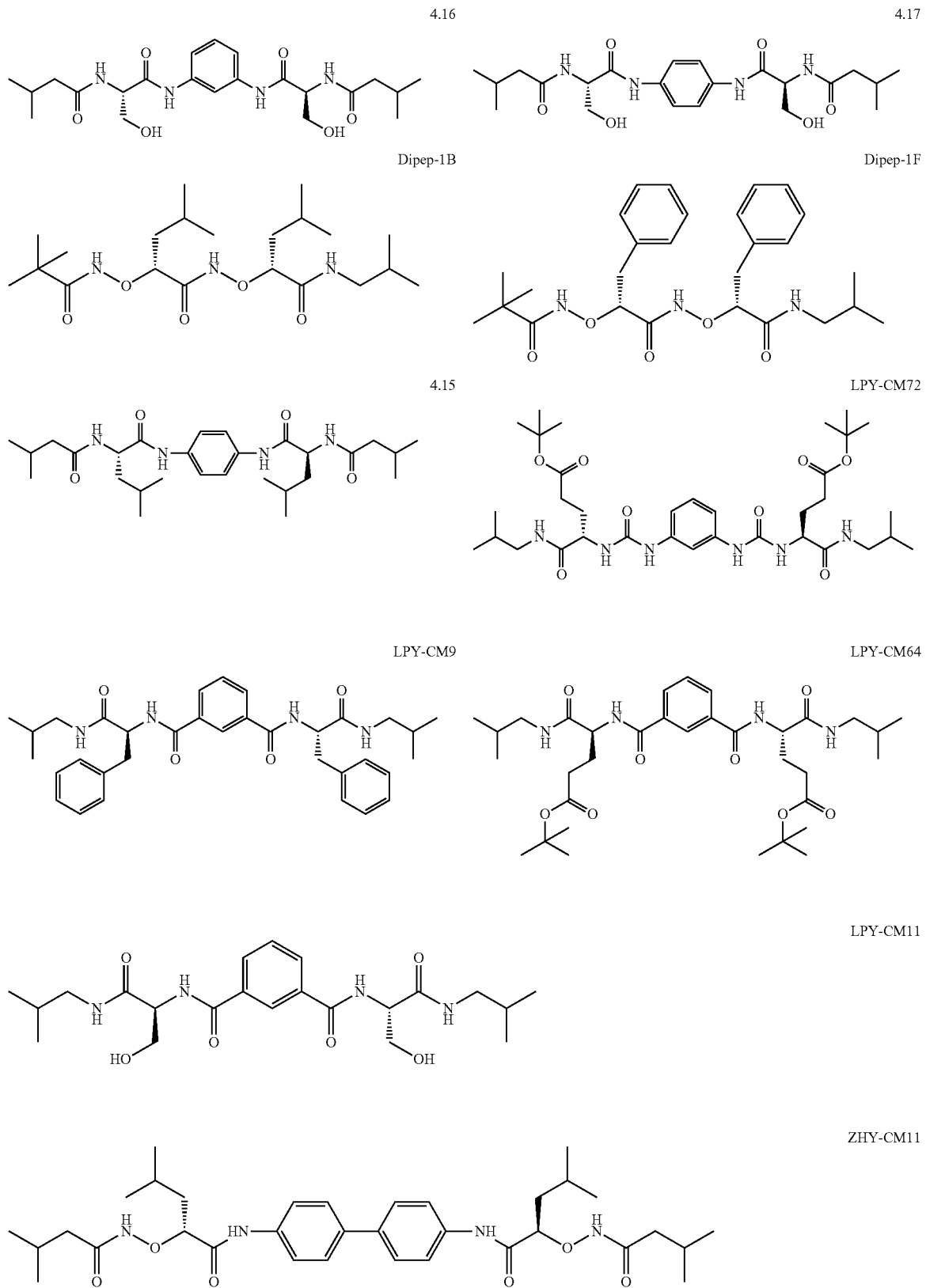

-continued
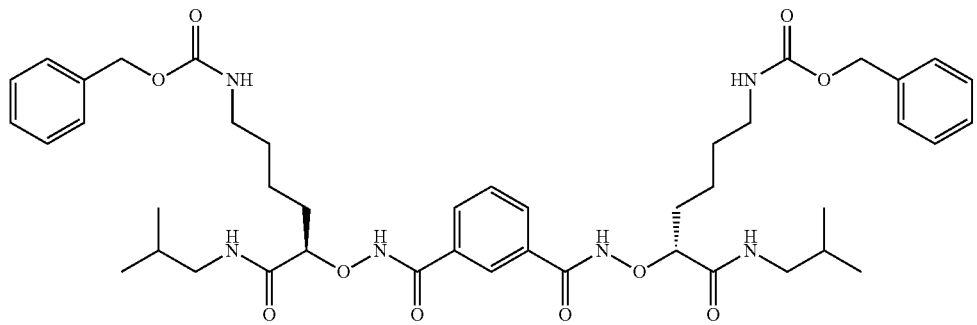
ZHY-CM23Cbz
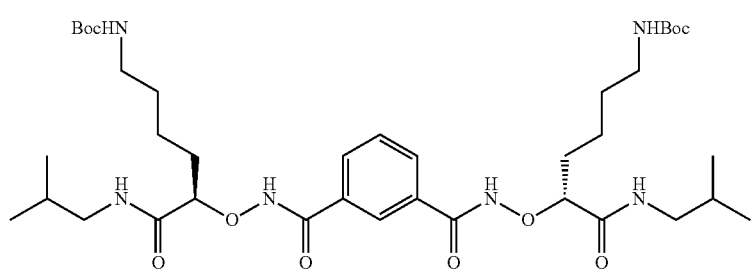
ZHY-CM23
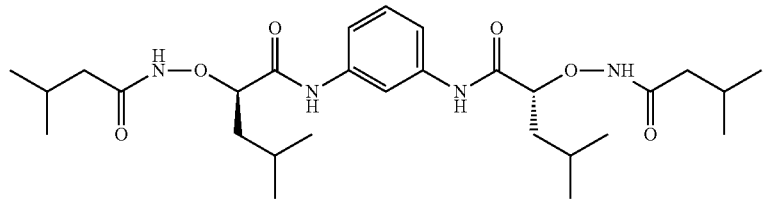
4.11
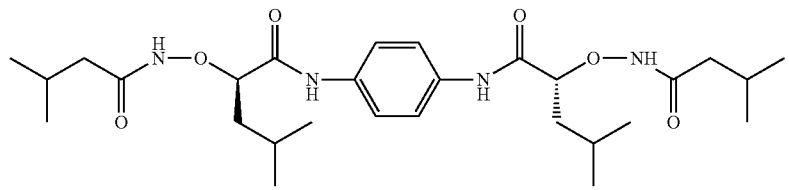
4.12
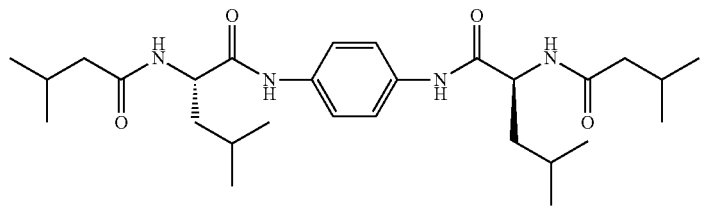
ZMY-CM13
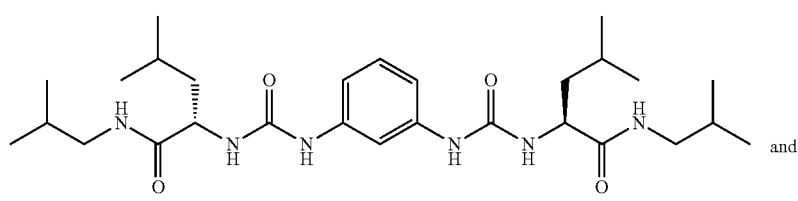
4.19
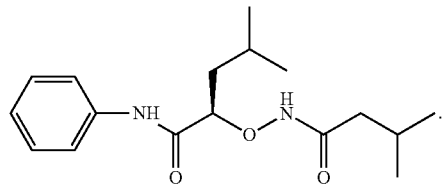
4.25

9. A self-assembling compound for the formation of ion channels in lipid bilayers or cell membranes having formula (I):

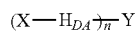 (I)

or a salt, solvate, polymorph or stereoisomer thereof,
wherein X is an unsubstituted or substituted hydrocarbyl or heterocyclyl;
n is an integer from 1 to 6;
Y is a monovalent, divalent, trivalent, tetravalent, pentavalent or hexavalent linking group formed by removing one, two, three, four, five and six hydrogen atoms respectively from an unsubstituted or substituted hydrocarbon or carbocycle; and
$H_{DA}$ is a divalent group having formula (X):

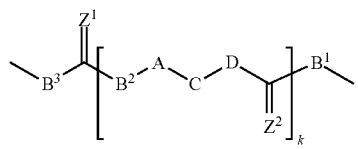 (X)

wherein each of $Z^1$ and $Z^2$ is independently O, S or $NR^1$;
each of A, $B^1$, $B^2$, $B^3$, C, and D is independently a bond, O, S, $NR^2$ or a substituted or unsubstituted $C_{1-10}$ alkylene; and
k is an integer from 1 to 20, where each of $R^1$ and $R^2$ is independently H, acyl, hydrocarbyl, carbocyclyl or heterocyclyl and at least one of $B^1$ and $B^2$ is NH.

10. The self-assembling compound of claim 9, wherein at least one of $Z^1$ or $Z^2$ is S or $NR^1$.

11. The self-assembling compound of claim 9, wherein at least one of A, $B^2$, C, and D is O or S.

12. The self-assembling compound of claim 9, wherein each of $B^1$, $B^2$, and $B^3$ is independently NH.

13. A composition, comprising a cell membrane and a plurality of molecules of the self-assembling compound of claim 9.

14. The composition of claim 13, wherein the cell membrane comprises a lipid bilayer.

15. The composition of claim 14, wherein the plurality of molecules self-assemble to form an anion channel across the thickness of the lipid bilayer.

16. The composition of claim 15, wherein the anion channel is a fluoride, chloride, bromide, iodide, nitrate, nitrite, sulfate, bisulfate, carbonate, bicarbonate, phosphate, hydrogen phosphate, dihydrogen phosphate or acetate channel.

17. The composition of claim 16, wherein the anion channel is a chloride channel.

18. A method of forming a synthetic anion channel in a cell membrane, the method comprising the step of combining the cell membrane with a plurality of molecules of the self-assembling compound of claim 9.

19. The method of claim 18, wherein the cell membrane comprises a lipid bilayer.

20. A method of modulating the flow of ions through a cell membrane, the method comprising the steps of forming an anion channel in the membrane from a plurality of molecules of the self-assembling compound of claim 9; and imposing an ion gradient or a membrane potential across the cell membrane.

21. The method of claim 20, wherein the cell membrane comprises a lipid bilayer.

22. A method of making a synthetic ion channel in a cell membrane comprising the steps of:
(a) providing a plurality of molecules of the self-assembling compound of claim 9; and
(b) forming molecular columns in the transverse direction of the membrane and between any two adjacent molecular columns by the self-assembling of the molecules through intermolecular hydrogen bonds in the lateral direction of the membrane.

23. The method of claim 22, wherein the cell membrane comprises a lipid bilayer.

24. A method of treating, managing or preventing a disease that is related to the dysfunction of chloride channel, the method comprising administering a plurality of molecules of a self-assembling compound of claim 9 or a pharmaceutically acceptable salt, solvate, polymorph or stereoisomer thereof.

25. The method of claim 24, wherein the disease is cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy or osteopetrose.

26. The method of claim 24, wherein the self-assembling compound or a pharmaceutically acceptable salt, solvate or stereoisomer thereof is inserted into the lipid bilayer of a cell of a mammal.

27. The method of claim 24, wherein the mammal is a human.

28. A pharmaceutical composition, comprising the self-assembling compound of claim 9 or a pharmaceutically acceptable salt, solvate, polymorph or stereoisomer thereof, and a pharmaceutically acceptable carrier.

29. The pharmaceutical composition of claim 28, further comprising at least an ingredient selected from the group consisting of excipients, moisturizers, diluents, metal stearates and combinations thereof.

30. The pharmaceutical composition of claim 28, which is in a single unit dosage form.

31. The pharmaceutical composition of claim 28, which is in a single unit dosage form suitable for inserting into the lipid bilayer of a mammalian cell.

32. An ion channel comprising a plurality of molecules of the self-assembling compound of claim 9, wherein the ion channel is in a cell membrane.

33. The ion channel of claim 32, wherein the ion channel is an anion channel.

34. The ion channel of claim 32, wherein the cell membrane comprises a lipid bilayer.

* * * * *